US009566251B2

(12) United States Patent
Burton et al.

(10) Patent No.: US 9,566,251 B2
(45) Date of Patent: *Feb. 14, 2017

(54) VOLATILE ANESTHETIC COMPOSITIONS AND METHODS OF USE

(71) Applicant: Board of Regents, The University of Texas System, Austin, TX (US)

(72) Inventors: Allen Burton, Houston, TX (US); Phillip C. Phan, Houston, TX (US); Hatice Ozsoy, Houston, TX (US); Christopher C. Capelli, Houston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/722,880

(22) Filed: Dec. 20, 2012

(65) Prior Publication Data
US 2013/0273141 A1    Oct. 17, 2013

Related U.S. Application Data

(62) Division of application No. 12/863,757, filed as application No. PCT/US2009/031707 on Jan. 22, 2009, now abandoned.

(60) Provisional application No. 61/011,898, filed on Jan. 22, 2008.

(51) Int. Cl.
*A61K 31/08* (2006.01)
*A61K 9/00* (2006.01)
*A61K 9/107* (2006.01)
*A61K 31/075* (2006.01)

(52) U.S. Cl.
CPC ............. *A61K 31/08* (2013.01); *A61K 9/0014* (2013.01); *A61K 9/0019* (2013.01); *A61K 9/0024* (2013.01); *A61K 9/0085* (2013.01); *A61K 9/107* (2013.01); *A61K 31/075* (2013.01)

(58) Field of Classification Search
None
See application file for complete search history.

(56) References Cited

U.S. PATENT DOCUMENTS

| 4,622,219 | A | * | 11/1986 | Haynes ..................... 424/450 |
| 4,725,442 | A |   | 2/1988  | Haynes |
| 4,744,989 | A |   | 5/1988  | Payne et al. |
| 4,879,062 | A |   | 11/1989 | Moore |
| 5,091,188 | A |   | 2/1992  | Haynes |
| 5,230,778 | A |   | 7/1993  | Gavlin et al. |
| 5,336,429 | A |   | 8/1994  | Barthelemy et al. |
| 5,416,071 | A |   | 5/1995  | Igari et al. |
| 5,874,469 | A |   | 2/1999  | Maniar et al. |
| 2003/0027833 | A1 |   | 2/2003 | Cleary et al. |
| 2004/0086556 | A1 |   | 5/2004 | Luo et al. |
| 2004/0127578 | A1 |   | 7/2004 | Trillo et al. |
| 2005/0287075 | A1 |   | 12/2005 | Dugger |
| 2006/0067952 | A1 |   | 3/2006 | Chen |
| 2006/0198891 | A1 |   | 9/2006 | Ravenelle et al. |
| 2007/0104796 | A1 | * | 5/2007 | Franks et al. ................. 424/600 |
| 2008/0119820 | A1 |   | 5/2008 | Phan et al. |
| 2008/0234389 | A1 |   | 9/2008 | Mecozzi et al. |
| 2011/0039944 | A1 |   | 2/2011 | Capelli et al. |
| 2011/0269843 | A1 |   | 11/2011 | Phan et al. |
| 2012/0171281 | A1 |   | 7/2012 | Spakevicius et al. |

FOREIGN PATENT DOCUMENTS

| CA | 2283227 | 9/1998 | |
| EP | 0 153 926 | 2/1991 | |
| JP | 60-501557 | 9/1985 | |
| JP | 2003-520769 | 7/2003 | |
| JP | 2006-504740 | 2/2006 | |
| JP | 2006-505611 | 2/2006 | |
| JP | 2010-504359 | 2/2010 | |
| WO | WO 85/00011 | 1/1985 | |
| WO | WO 00/72820 | 12/2000 | |
| WO | WO 2004/032858 | 4/2004 | |
| WO | WO 2004/043428 | 5/2004 | |
| WO | WO 2005009510 A2 * | 2/2005 | ......... G01N 33/5082 |
| WO | WO 2005-034966 | 4/2005 | |
| WO | WO 2008-036858 | 3/2008 | |
| WO | WO 2008/036858 | 3/2008 | |

OTHER PUBLICATIONS

Office Action issued in Chinese Application No. 200980110827.5, issued Aug. 29, 2012 (English language translation only).
Office Action issued in European Application No. EP 09704014, mailed Apr. 19, 2012.
Office Action issued in U.S. Appl. No. 12/863,757, mailed Jun. 22, 2012.
Office Action issued in U.S. Appl. No. 12/863,757, mailed Mar. 27, 2012.
PCT International Preliminary Report on Patentability issued in International Application No. PCT/US2009/031707, issued Jul. 27, 2010.
PCT International Search Report issued in International Application No. PCT/US2009/031707, mailed Jun. 1, 2009.
Garcia-Fernandez et al., "Clinical actions of subarachnoid sevoflurane administration in vivo: a study in dogs," *British Journal of Anaesthesia*, 95(4):530-534, 2005.
Haynes and Kirkpatrick, "Long duration local anesthesia with lecithin-coated microdroplets of methoxyflurane: studies with human skin," *Regional Anesthesia*, 16(3):173-180, 1991. Abstract only.

(Continued)

*Primary Examiner* — Frederick Krass
*Assistant Examiner* — Michael P Cohen
(74) *Attorney, Agent, or Firm* — Parker Highlander PLLC

(57) ABSTRACT

The present invention provides methods for reducing pain in a subject in need thereof by delivering a volatile anesthetic in a solution or an emulsion that can additionally include an extractive solvent in an amount effective to reduce pain without substantially interfering with motor function. Chronic or acute pain may be treated, or the volatile anesthetic may be delivered as a regional anesthetic to a subject to anesthetize a portion of the subject prior to surgery. Dosing regimes including a one-time administration, continuous and/or periodic administration are contemplated.

6 Claims, 5 Drawing Sheets

(56) References Cited

OTHER PUBLICATIONS

Office Action issued in Australian Application No. 2009206391, mailed Apr. 3, 2013.
Office Action issued in Chinese Application No. 200980110827.5, mailed Jul. 4, 2013.
Office Action issued in European Applicatio No. 09 704 014.1, mailed Mar. 31, 2014.
Office Action issued in Japanese Application No. 2010-544419, mailed May 1, 2014, and English language translation thereof.
Office Action issued in Japanese Application No. 2010-544419, mailed May 13, 2013, and English language translation thereof.
Office Action issued in Canadian Application No. 2,712,516, mailed Feb. 20, 2015.
Haynes et al., "Long duration local anesthesia with lecithin-coated microdroplets of methoxyflurane: studies with human skin," *Regional Anesthesia*, 16:173-180, 1991.

* cited by examiner

VOLATILE ANESTHETIC COMPOSITIONS AND METHODS OF USE

This application is a divisional of U.S. application Ser. No. 12/863,757, filed as International Application No. PCT/US2009/031707 on Jan. 22, 2009, which claims priority to U.S. Provisional Application No. 61/011,898, filed on Jan. 22, 2008. The entire content of each of the above-referenced disclosures is specifically incorporated herein by reference.

BACKGROUND OF THE INVENTION

Millions of people suffer from pain. The pain may be minor, such as headaches, acute lower back pain, and acute muscle pain, or severe, such as chronic pain. Chronic pain may be associated with cancer treatment, HIV, diabetes, or other conditions. Chronic pain can be difficult to treat, with many chronic pain sufferers noting that their pain is not well controlled with current pain medications or that their medications have significant associated adverse effects (for example, nausea and vomiting, dependence, tolerance, etc.).

In an attempt to address the problem of chronic pain management, intrathecal infusion pumps and neurostimulators have been developed. Intrathecal infusion pumps are aimed at continuous, or near continuous delivery of liquid analgesic agents. Many of these infusion pumps are totally implantable, which helps to reduce the risk of infection when compared to the long-term use of external systems. The infusion pump may also be programmable to allow patients or their clinicians to adjust dosing amounts or daily delivery schedule, helping to meet a patient's changing needs.

Neurostimulators are available in various forms and stimulate nerves to relieve pain. Both intrathecal pumps and neurostimulators have drawbacks, including the onset of tolerance, with the treatments becoming less effective over time.

Various approaches for inducing anesthesia or analgesia are known. Systemic delivery of a general anesthetic renders a patient unconscious and unaware of the surgery. In contrast, anesthetics may be applied regionally, for example, to the spine, to the spinal cord (intrathecally or epidurally), or near a nerve in a nerve block to anesthetize only a portion of the patient's body. For general anesthesia, delivery of a general anesthetic to a patient prior to surgery is typically performed using an initial i.v. injection of an induction agent followed by intubation and administration of an inhaled anesthetic gas. It is worthwhile to note that the mechanism of action for general anesthesia is still not completely understood.

Considerable negative side effects may result from administration of general anesthesia. A tube has to be placed into the trachea, necessary to protect against vomiting, which can result in trauma to the upper airway. Many patients report postoperative hoarseness and tenderness of the mouth and throat. In addition, the dose of gases required to reach the targeted neural organs can have an adverse affect on the non-targeted organs, especially the heart, with an increased risk of cardiopulmonary morbidity during general anesthesia. Especially in the elderly, there is substantial evidence for prolonged cognitive dysfunction following general anesthesia (Moller et al., 1988, Lancet., 351:857-861). Additionally, regional anesthetic techniques appear to lead to less overall morbidity and mortality from cardiopulmonary causes as compared to general anesthesia (Rasmussen et al., 2003, Acta Anaesthesiologica Scandinavica, 47:260-266; Rogers et al., 2000, BMJ, 321:1-12).

Certain risks are also associated with inhalation administration of a volatile anesthetic, for example, during general anesthesia. Volatile anesthetic compositions formulated for inhalation generally have relatively low boiling points and high vapor pressures. Older, volatile anesthetic compositions (including ether and cyclopropane) are often flammable or explosive in both their liquid and vapor states, with newer agents much less see (see Williams and Lemke, 2002, Foye's Principles of Medicinal Chemistry, Lippincott Williams & Wilkins, NY). Further, inhalation of vapors by health care personnel in trace amounts have unknown health consequences, and have been the subject of much debate. In the larger amounts used in pediatric operating room's, large amounts of gas can escape during inhalational induction and can cause frank drowsiness or headaches, which is not desirable in an operating room environment. Thus, substantial care must be taken to safely handle volatile anesthetics (including venting of operating rooms) in order to minimize both the risk of inhalation by medical personnel and the risk of fire and care must be taken to try to ensure that there is little or no release of the volatile anesthetic into the atmosphere at all stages of handling.

Clearly, there exists a need for improved methods for pain management and local and regional anesthesia. Further, there exists a need for volatile anesthetic compositions that have reduced risks, as described above, associated with their use. There is also a need for methods for delivering such improved volatile anesthetic compositions for treating pain without substantially interfering with motor function. The current invention fulfills these needs.

SUMMARY OF THE INVENTION

The present invention contemplates compositions and methods for reducing pain in a subject in need thereof by delivering to the subject by a route other than orally, intravenously, or by inhalation a volatile anesthetic. The present invention overcomes limitations in the prior art by providing improved volatile anesthetic compositions and methods for administering volatile anesthetics and reducing pain in a subject, such as a human or animal patient or laboratory animal such as a mouse or rat, in need of such pain reduction. In one embodiment, the present invention provides a volatile anesthetic composition comprising a volatile anesthetic dissolved in a aqueous-based solution, wherein the solution further comprises a pharmaceutically acceptable extractive solvent (e.g., DMSO, etc.). In another embodiment, the present invention provides a volatile anesthetic composition comprising a volatile anesthetic in an emulsion. In still another embodiment, the present invention provides a volatile anesthetic composition comprising a volatile anesthetic in a liposome or in a microdroplet.

The presence of an extractive solvent in the composition comprising the volatile anesthetic may provide substantial advantages, including improving the physical characteristics, pharmacological properties, and/or the ease of use of the volatile anesthetic. The extractive solvent may interact with the volatile anesthetic in a non-azeotropic fashion to effectively reduce vaporization or evaporation of the volatile anesthetic. In this way, the shelf-life, durability, and/or ease of use of a volatile anesthetic composition may be improved. The presence of an extractive solvent in the volatile anesthetic composition may also improve the ease of mixing the composition prior to administration. Additionally, the pharmacokinetics of the volatile anesthetic may be altered by the presence of an extractive solvent to provide improved pain relief. For example, without wishing to be bound by any theory, the inventors anticipate that the extractive solvent may function in certain embodiments as a reservoir for the volatile anesthetic to maintain the volatile anesthetic in a particular region more effectively and/or help deliver the volatile anesthetic to site(s) of action. Reduced volatility of the volatile anesthetic may also improve the ease of handling the volatile anesthetic compositions. Further, the reduced vaporization of a volatile anesthetic in the composition, due to the presence of an extractive solvent, may also reduce concerns regarding a possible risk of fire and/or inhalation by medical personnel.

It is understood that the methods of the invention include administration of the volatile anesthetic compositions by a route other than orally, intravenously, or by inhalation. The methods preferably comprise the local or regional delivery, such as, for example, transdermal, topical, mucosal, buccal, rectal, vaginal, intramuscular, subcutaneous, intrathecal or epidural delivery, of a volatile anesthetic composition to the subject in an amount effective to reduce chronic or acute pain. In other embodiments, a volatile anesthetic composition of the present invention may be administered topically in an amount sufficient to reduce pain. More specifically, the inventors have discovered that, in certain embodiments, volatile anesthetic compositions of the present invention may be administered topically to a human subject to achieve local pain reduction. It should be understood, that as used herein, the phrase "pain reduction" is intended to cover pain reduction as a result of anesthesia, analgesia, and/or the inhibition of neural impulses involved in pain perception, e.g., via partial nerve conduction block. In certain embodiments, the volatile anesthetic compositions of the invention may be delivered to a portion of the subject in an amount and in a manner effective to reduce pain. In other embodiments, the compositions of the invention may be delivered to a portion of the subject in an amount and in a manner effective to reduce pain without substantially interfering with motor function of the subject.

The present invention has several substantial advantages over previously used methods for regional anesthesia. These advantages include: (1) the volatile anesthetics of the present invention are rapidly titratable, thus administration of a volatile anesthetic according to the present invention can result in a very quick onset of analgesia or regional anesthesia. (2) The present invention allows for the quick dissipation of the volatile anesthetics after administration; thus the anesthesia or analgesia may be rapidly ended. These properties are of particular value to a practitioner, as it may be desirable for a practitioner to quickly alter the dosing of a regional anesthesia or analgesia as desired. (3) Certain drugs presently used for regional anesthesia may not be effectively used on various individuals for a variety of reasons, including tolerance, drug interactions, paradoxical responses, etc. Additionally, (4) the volatile anesthetics of the present invention are generally non-opioid compounds, which provides various benefits for a practitioner, as opioids possess certain disadvantages, including tolerance, drug interactions, and dependence etc.

Various extractive solvents may be used with the present invention. For example, dimethyl sulfoxide (DMSO), N-methyl-2-pyrrolidone (NMP), dimethylisosorbide, ethanol, propanol, or isopropanol may be the extractive solvent. The extractive solvent may comprise from about 0.1% to about 75% of the composition, 25% to about 75% of the composition, 10% to about 50% of the composition, from about 0.1% to about 25% of the composition, or from about 25% to about 50% of the composition.

An aspect of the present invention relates to a method for reducing pain in a subject in need of such pain reduction comprising regionally or locally delivering to the subject a volatile anesthetic composition in an amount effective to reduce pain. If the administration is intrathecal or epidural, then the composition may be free or essentially free of a lipid emulsion. In preferred embodiments, the volatile anesthetic is delivered by routes other than intravenously in that intravenous delivery could potentially give rise to general anesthesia that, while not specifically excluded from the present invention, is not a preferred aspect. Preferred volatile anesthetics are the halogenated ether anesthetics. The volatile anesthetic composition may preferably be delivered intrathecally, epidurally, or in a nerve block procedure, to relieve, for example, chronic pain or acute pain. In certain embodiments, the volatile anesthetic composition may be administered locally or topically prior to a procedure such as a venipuncture, an injection (e.g., Botox™), a peripheral venous cannulation, incision, hair removal, tattoo application and removal, mammography, or other procedure; in other embodiments, the volatile anesthetic composition may be administered via non-topical routes. In certain embodiments, the volatile anesthetic composition may be delivered to the subject to anesthetize the subject prior to a surgery.

The volatile anesthetic may be a halogenated volatile anesthetic selected from the group consisting of isoflurane, halothane, enflurane, sevoflurane, desflurane, methoxyflurane, and mixtures thereof. In certain embodiments, isoflurane is used. The volatile anesthetic composition can be prepared with a volatile anesthetic in a concentration of about 5 ng/ml to about 100 ng/ml. The volatile anesthetic may comprise from about 0.1% to about 15% v/v, 1% to about 75% v/v, 1% to about 50% v/v, 5% to about 50% v/v, 5% to about 75% v/v, from about 10% to about 50% v/v, or about 10% v/v volatile anesthetic in the composition. When administered epidurally or intrathecally it is desirable to achieve a concentration of from about 250 ng/ml to about 50,000 ng/ml of the volatile anesthetic in the spinal fluid. The delivery of the volatile anesthetic composition may be continuous, periodic, a one-time event, or the volatile anesthetic composition may be both periodically administered and continuously administered to the subject on separate occasions.

The reduction of pain may comprise elimination of pain perception of a portion of the body of the subject. In certain embodiments, the compositions of the invention may be delivered to a portion of the subject in an amount and in a manner effective to reduce pain without substantially interfering with motor function of the subject, for example, by varying the dosage, amount, concentration, frequency of administration, and/or timing of administration.

Preferably, in that the compositions of the invention are intended for administration by a route other than orally, intravenously, or by inhalation, the composition comprising the volatile anesthetic is sterile. This can be achieved by ensuring that all starting materials are sterile and maintaining them under sterile conditions prior to administration.

It is contemplated that any embodiment discussed in this specification can be implemented with respect to any method or composition of the invention, and vice versa. Furthermore, any of the compositions of the invention described herein can be used to achieve any of the methods of the invention described herein.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

DETAILED DESCRIPTION OF THE INVENTION

Figure 1:
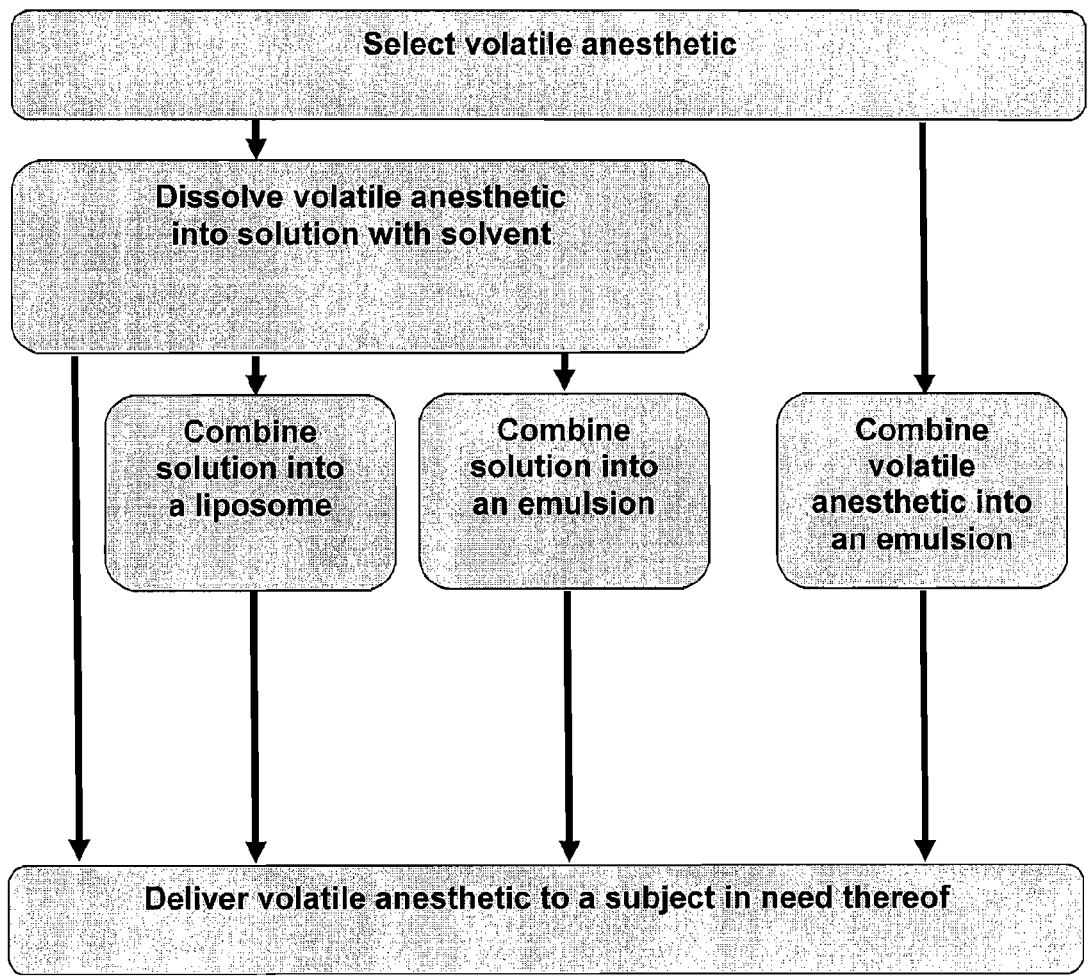
FIG. 1 depicts a flowchart representing general methods for making compositions for the delivery of an volatile anesthetic to a subject.

While compounds utilized as a general anesthetic reduce pain, at least in part, by producing a loss of consciousness, local anesthetics reduce pain by producing a loss of sensation or sensory blockade in a localized area or region of a subject. The mechanism by which local anesthetics reduce pain, while not having been determined definitively, is generally thought to involve the ability to interfere with the initiation and/or transmission of nerve impulses primarily via sodium channel blockade. In certain embodiments, the present invention may be used to reduce or eliminate pain in a subject without also causing a loss of consciousness of the subject. In other embodiments, the present invention may be used to reduce or eliminate pain in a subject without also substantially interfering with motor function of the subject.

The present invention provides improved volatile anesthetic compositions and methods for administering volatile anesthetics and reducing pain in a subject, such as a human or animal patient or laboratory animal such as a mouse or rat, in need of such pain reduction. In certain embodiments, the present invention provides a composition comprising a volatile anesthetic dissolved in an aqueous-based solution, wherein the solution further comprises a pharmaceutically acceptable extractive solvent, for example, but not limited to, DMSO. In certain embodiments, the present invention provides a composition comprising a volatile anesthetic dissolved in a aqueous-based solution, wherein the solution comprises a pharmaceutically acceptable extractive solvent, for example, but not limited to, DMSO, and wherein the solution is a component of an emulsion. In certain additional embodiments, the present invention provides a composition comprising a volatile anesthetic dissolved in a aqueous-based solution, wherein the solution comprises a pharmaceutically acceptable extractive solvent, for example, but not limited to, DMSO, and wherein the solution is a component of a liposome. In yet other embodiments, the present invention provides a composition comprising a volatile anesthetic dissolved in a aqueous-based solution. In certain embodiments, the present invention provides a composition comprising a volatile anesthetic dissolved in a aqueous-based solution, and wherein the solution is a component of an emulsion. In additional embodiments, the present invention provides a composition comprising a volatile anesthetic dissolved in a aqueous-based solution, and wherein the solution is a component of a liposome.

The presence of an extractive solvent in the composition comprising the volatile anesthetic may provide substantial advantages, including improving the physical characteristics, pharmacological properties, and/or the ease of use of the volatile anesthetic composition. The extractive solvent may interact with the volatile anesthetic (for example, isoflurane) in a non-azeotropic fashion to effectively reduce vaporization or evaporation of the volatile anesthetic. In this way, the shelf-life, durability, and/or ease of use of a volatile anesthetic composition may be improved. The presence of an extractive solvent in the volatile anesthetic composition may also improve the ease of mixing the composition prior to administration. Additionally, the pharmacokinetics of the volatile anesthetic may be altered by the presence of an extractive solvent to provide improved pain relief. For example, without wishing to be bound by any theory, the inventors anticipate that the extractive solvent may function in certain embodiments as a reservoir for the volatile anesthetic to maintain the volatile anesthetic in a particular region more effectively and/or help deliver the volatile anesthetic to site(s) of action. Similarly, in certain embodiments where the volatile anesthetic solution is a component of an emulsion or of a liposome, the emulsion or the liposome may function as a reservoir for the volatile anesthetic to retain the volatile anesthetic in a particular region more effectively and/or help deliver the volatile anesthetic to site(s) of action. Reduced volatility of the volatile anesthetic in solution may also improve the ease of handling the volatile anesthetic compositions. Further, the reduced vaporization of a volatile anesthetic in solution due to the presence of an extractive solvent may also reduce concerns, as described above, regarding a possible risk of fire and/or inhalation by medical personnel.

An aspect of the present invention relates to a method for reducing pain in a subject in need thereof comprising regionally or locally delivering to the subject by a route other than orally, intravenously or by inhalation, a volatile anesthetic dissolved in a solution comprising an extractive solvent in an amount effective to reduce pain. In preferred embodiments, the volatile anesthetic is delivered by routes other than intravenously in that intravenous delivery could potentially give rise to general anesthesia that, while not specifically excluded from the present invention, is not a preferred aspect. Preferred volatile anesthetics are the halogenated ether anesthetic dissolved in an aqueous, pharmaceutically acceptable solution. In certain embodiments, the volatile anesthetic can be a component of an emulsion or of a liposome.

It is understood that the invention does not include administration of the volatile anesthetic to a subject orally, intravenously or by inhalation of the volatile anesthetic vapor alone. The methods preferably comprise the local or regional delivery, such as, for example, transdermal, topical, mucosal, buccal, rectal, vaginal, intramuscular, subcutaneous, perineural infiltration, intrathecal or epidural delivery, of a volatile anesthetic in an aqueous-based solution, which in some embodiments can be a component of an emulsion or of a liposome, to the subject in an amount effective to reduce chronic or acute pain. In other embodiments, a composition of the present invention may be administered topically in an amount sufficient to reduce pain. In certain embodiments, the volatile anesthetic may be delivered to the subject to anesthetize the subject prior to a surgery or other medical procedure. In certain embodiments, the compositions of the invention may be delivered to a portion of the subject in an amount and in a manner effective to reduce pain. In other embodiments, the compositions of the invention may be delivered by a route other than orally, intravenously or by inhalation, to a portion of the subject in an amount and in a manner effective to reduce pain without substantially interfering with motor function of the subject.

The present invention has several substantial advantages over previously used methods for regional anesthesia. These advantages include: (1) the volatile anesthetics of the present invention are rapidly titratable, thus administration of a volatile anesthetic according to the present invention can result in a very quick onset of analgesia or regional anesthesia. (2) The present invention allows for the quick dissipation of volatile anesthetics after administration; thus the anesthesia or analgesia may be rapidly ended. These properties are of particular value to a practitioner, as it may be desirable for a practitioner to quickly alter the dosing of a regional anesthesia or analgesia as desired. (3) Certain drugs presently used for regional anesthesia may not be effectively used on various individuals for a variety of reasons, including tolerance, drug interactions, paradoxical responses, etc. Additionally, (4) the volatile anesthetics of the present invention are generally non-opioid compounds, which provides various benefits for a practitioner, as opioids possess certain disadvantages, including respiratory depression, pruritis, addiction, tolerance, drug interactions, and dependence etc.

In certain embodiments, a volatile anesthetic in solution is delivered to anesthetize a portion of the subject prior to a surgery or other medical procedure. The volatile anesthetic may be a halogenated volatile anesthetic selected from the group consisting of isoflurane, halothane, enflurane, sevoflurane, desflurane, methoxyflurane, xenon and mixtures thereof. Many of these agents are racemic mixtures. In some embodiments, the racemic mixtures can be used. In other embodiments, only the d-isomer or the l-isomer of an agent can be used (for examples, see U.S. Pat. Nos. 5,114,715, 5,114,714 and 5,283,372). In certain embodiments, isoflurane is used. The solution, such as an isoflurane solution, may be prepared in a concentration of about 5 ng/ml solution to about 100 ng/ml solution. The solution may comprise from about 1% to about 99% v/v, from about 5% to about 50% v/v, or about 10% v/v volatile anesthetic in solution. The volatile anesthetic may be isoflurane and/or the solution may be water, saline or artificial cerebrospinal fluid. In certain embodiments, the solution can be a component of an emulsion, which can further comprise an extractive solvent. In other embodiments, the solution can be a component of an liposome, which can further comprise an extractive solvent. When administered epidurally or intrathecally it is desirable to achieve a concentration of from about 250 ng/ml to about 50,000 ng/ml of active agent in the spinal fluid. The delivery of the volatile anesthetic composition may be continuous, periodic, a one-time event, or the volatile anesthetic composition may be both periodically administered and continuously administered to the subject on separate occasions. The reduction of pain may comprise the reduction or elimination of pain perception of a portion of the body of the subject. The reduction of pain may comprise the reduction or elimination of pain sensation of a portion of the body of the subject. The reduction or elimination of pain may be achieved without also substantially interfering with motor function.

In some embodiments, the compositions of the invention may be delivered by a route other than orally, intravenously or by inhalation, to a portion of the subject in an amount and in a manner effective to reduce pain without substantially interfering with motor function of the subject, for example, by varying the dosage, amount, concentration, frequency of administration, and/or timing of administration. Tests useful for the evaluation of motor function include, for example, but are not limited to, the Minnesota Rate of Manipulation (MRM) test (Fleishman, 1964, Abilities and motor skill. In: The structure and measurement of physical fitness Prentice-Hall, Inc.: Englewood Cliffs, N.J., 1964, pp. 23-24), the Upper Extremity Function Test (DEFT) (Carroll, 1965, J Chron Dis 18: 479-491), the Purdue Pegboard test (Tiffin et al., 1948, J Appl Psychol 32: 234-247), the Jebsen test of hand function (Jebsen et al., 1969, Arch Phys Med Rehab 50: 311-319), the Nine-Hole Peg test (Kellor et al., 1971, Am J Occup Ther 25: 77-83), the Smith hand function evaluation (Smith, 1973, Am J Occup Ther 27: 244-251), the Box and Block Test (BBT) (Holser et al., 1960, Box and Block test. In: Cromwell F S (ed) Occupational therapists manual for basic skills assessment: primary prevocational evaluation Fair Oaks Printing Company Pasadena, Calif., pp. 29-31), the Physical Capacities Evaluation of Hand Skill (PCE) (Bell et al., 1976, Am J Occup Ther 30: 80-86), the Action Research Arm (ARA) test (Lyle, 1981, Int J Rehabil Res 4: 483-492), the Sollerman hand function test (Sollerman et al., 1995, Scand J Plast Reconstr Surg Hand Surg 29: 167-176), Lower Extremity MOtor COordination Test (LEMOCOT) (Desrosiers et al., 2005, Arch Phys Med Rehabil 86, 993-98), the Fugl-Meyer Assessment (Fugl-Meyer et al., 1975, Scand J Rehabil Med 7:13-31), Berg Balance Scale (Berg et al., 1995, Scand J Rehabil Med 27:27-36; Berg et al., 1989, Physiother Can 41:304-11, Berg et al, 1992, Arch Phys Med Rehabil 73:1073-80; Stevenson et al., 1996, Arch Phys Med Rehabil 77:656-62), 5-meter walking test (5MWT) (Salbach et al., 2001, Arch Phys Med Rehabil 82:1204-12), 2-minute walking test (Wade, 1992, Measurement in neurological rehabilitation. New York: Oxford Univ Pr; Guyatt et al., 1984, Thorax 39:818-22), and the Functional Autonomy Measurement System (Hebert, 1988, Age Ageing 17:293-302), all of which references are incorporated herein in their entirety. The motor function of a subject is not substantially interfered with when the subject's motor function, when measured after delivery of the compostions of the invention, is at least about 40% of that of a comparator value, preferably at least about 60% of that of a comparator value, more preferably at least about 75% of that of a comparator value, and even more preferably about 90% of that of a comparator value. Useful comparator values include, but are not limited to, a value obtained by measuring the subject's motor function prior to administration of the compositions of the invention, a value obtained by measuring the motor function of an untreated but otherwise similarly-situated subject, a value obtained by measuring the motor function of an untreated control subject, or a value known or derived from historical norms or averages.

Preferably, in that the solution is intended for administration by a route other than orally, intravenously or by inhalation, the aqueous solution comprising the volatile anesthetic is sterile. This can be achieved by ensuring that all starting materials are sterile and maintaining them under sterile conditions prior to administration. This can also be achieved by incorporation of an antimicrobial filter as has been done with other types of infusions (see, for example, U.S. Pat. No. 5,695,490). As for the underlying aqueous solution, the nature of the solution is not believed to be critical, and solutions such as normal saline or even solutions formulated to mimic natural body fluids, such as artificial cerebrospinal fluids, are contemplated.

Yet another aspect of the present invention involves a sealed container comprising an volatile anesthetic solution of the present invention. The interior of the container may be sterile. The container may comprise a rubber stopper which can be easily pierced by an injection needle. The container may comprise the chamber portion of a syringe. The container may comprise a drip chamber. The drip chamber may be coupled to a catheter. The catheter may be an epidural catheter or an intrathecal catheter. The container can be a syringe, a plastic bag, a collapsible plastic bag, a glass bottle, a glass ampoule, or a plastic bottle. The container may be coupled to an infusion pump. The infusion pump may be an intrathecal pump, an epidural delivery infusion pump, or a patient control analgesia (PCA) pump. The infusion pump may be programmable.

The present invention overcomes limitations in the art by providing improved volatile anesthetic compositions comprising a volatile anesthetic dissolved in an aqueous-based solution, wherein the solution further comprises a pharmaceutically acceptable extractive solvent. The presence of the extractive solvent may provide certain advantages for the volatile anesthetic composition, including a reduction in the volatile anesthetic vapors emitted from the solution (for example, reducing risks associated with the flammability of the vapors and/or inhalation by medical personnel), improvements in the shelf-life or durability of the composition, and/or improved pharmacokinetics of the volatile anesthetic composition. For example, the extractive solvent may interact with the volatile anesthetic (for example, isoflurane) in a non-azeotropic fashion to effectively reduce vaporization or evaporation of the volatile anesthetic. In this way, the shelf-life and/or durability of a volatile anesthetic in solution may be improved. Additionally, the pharmacokinetics of the volatile anesthetic may be altered to provide improved pain relief. For example, without wishing to be bound by any theory, the inventors anticipate that the extractive solvent may function in certain embodiments as a reservoir for the volatile anesthetic to maintain the volatile anesthetic in a particular region more effectively and/or help deliver the volatile anesthetic to site(s) of action.

The present invention also provides methods for using such volatile anesthetic compositions for reducing pain in a subject in need thereof. Specifically, although volatile anesthetics have been delivered by inhalation to produce general anesthesia, the inventors have discovered that the volatile anesthetics of the invention may be dissolved in a solution and delivered regionally or locally (for example, transdermally, topically, muco sally, buccally, rectally, vaginally, intramuscularly, subcutaneously, perineurally, intrathecally, epidurally, or in a nerve block, etc.) to reduce or inhibit pain or block or inhibit pain perception. Further, by varying the dosage, amount, concentration, frequency of administration, and/or timing of administration, for example, of a volatile anesthetic in solution, or a volatile anesthetic emulsion, a reduction of pain can be achieved without at the same time substantially interfering with motor function in the subject. In general, the methods may involve the delivery of a volatile anesthetic, which in certain embodiments can be a component of a solution, an emulsion, or a liposome, to the subject in an amount effective to reduce pain. The present invention may be used for pain management of chronic or acute pain. In other embodiments, the volatile anesthetic may be delivered to a subject to anesthetize at least a portion of the subject prior to a surgery or other medical procedure.

Extractive Solvents

The volatile anesthetic compositions of the present invention may contain a solvent, such as an extractive solvent, in combination with a volatile anesthetic. The phrase "extractive solvent," as used herein, refers to a solvent which may interact with a volatile anesthetic in the compositions of the invention to reduce the volatility of the volatile anesthetic without chemically reacting to the anesthetic. Certain extractive solvents interact in a non-azeotropic fashion with a volatile anesthetic; nonetheless, the term "extractive solvent," as used herein, may include certain compounds which interact with a volatile anesthetic to form an azeotropic or pseudoazeotropic solution as long as the vapor pressure or evaporation of the volatile anesthetic from the solution is reduced. As described below, various extractive solvents are envisioned for use with the present invention, e.g., DMSO, NMP, etc. The exact concentration of an extractive solvent may be determined empirically and may vary according to the specific volatile anesthetic used. In certain embodiments, the extractive solvent will be present in the composition in an amount effective to reduce volatility of the volatile anesthetic in the composition. Particular care should also be taken to choose a concentration of an extractive solvent which results in little or no toxicity when administered. It will be understood that, although certain extractive solvents may exhibit properties which might be used in various separation procedures (e.g., extractive distillation), extractive solvents according to embodiments of the present invention are preferably included in pharmacological mixtures or solutions comprising a volatile anesthetic in order to reduce the volatility of, rather than "extract," the volatile anesthetic.

Including an extractive solvent in an anesthetic composition may increase the ease with which one can mix the solution prior to administration. For example, in certain embodiments, sonication of the anesthetic solution prior to administration is not required when an extractive solvent is included in the volatile anesthetic composition. This advantage may be particularly useful in instances (e.g., chronic administration) where the presence of a sonicator could be noisy or distracting, such as an operating room, and the elimination in the noise of a sonicator may also create an improved environment for a conscious patient receiving a volatile anesthetic composition, e.g., chronically or intermittently for pain relief. Eliminating the need for a sonicator, or other similar device, may also be particularly useful for reducing costs associated with administration of an volatile anesthetic composition according to the present invention. The reduction in the bulk associated with the presence of a sonicator can beneficially improve patient mobility. For example, in instances where a patient may receive repeated administrations of an anesthetic composition via a pump for analgesia, the reduced amount of equipment can improve mobility since the patient is not required to additionally move a sonicator.

Extractive solvents are known in the art and are typically used in extractive distillation for separating compounds with similar boiling points by retarding the vapor pressure of the principal component, thereby making possible an efficient separation which would not at all occur in the absence of such solvent. For example, U.S. Pat. No. 5,230,778 describes the purification of isoflurane by extractive distillation using extractive solvents such as dimethylformamide. U.S. Pat. No. 5,336,429 describes solvents for cleaning electronic components and for degreasing metals comprising isoflurane and a lower alcohol or an ester, although these compositions are described as azeotropic mixtures with virtually constant boiling points. In contrast, the present invention provides pharmaceutical preparations, e.g., for inducing analgesia and/or regional anesthesia. Certain extractive solvents known in the art, such as acetone as described in U.S. Pat. No. 5,230,778, may be sufficiently toxic to limit their inclusion in pharmaceutical preparations at higher concentrations.

In certain embodiments, an extractive solvent may interact as an azeotropic mixture with an anesthetic and reduce the volatility of the anesthetic. For example, ethanol may interact in an azeotropic fashion with a volatile anesthetic as described in U.S. Pat. No. 5,230,778.

Various concentrations of an extractive solvent may be used with the present invention. For example, a composition of the present invention comprising a volatile anesthetic may comprise about 0.1%-99%, 0.1%-60%, 5%-50%, 10%-40%, 5%-25%, 10%-30%, 10%-25%, 25%-50%, 10%-75%, 25%-75%, 10%-65%, 25%-65%, 10%-60%, 25%-60%, 0.1%, 1%, 5%, 10%, 20%, 25%, 30%, 35%, 40%, 45%, 50%, 55%, 60%, 65%, 70%, 75%, 80% or any range derivable therein, of an extractive solvent.

In certain embodiments, the extractive solvent is dimethylsulfoxide (DMSO) or N-methyl-2-pyrrolidone (NMP). In other embodiments, an extractive solvent such as dimethylformamide, dimethylacetamide, or dimethylisosorbide may be used. In instances where acetone is used, care should be taken to choose an appropriate dose in order to minimize any possible toxicity.

In various embodiments, it is envisioned that a medically acceptable alcohol, such as ethanol, propanol, or isopropanol may be used. In these embodiments, the concentration of the alcohol used is sufficiently dilute in solution such that little or no neuron death occurs as a result of injection of the solution near a nerve.

A single extractive solvent or multiple extractive solvents may be present in an volatile anesthetic composition of the present invention. For example, in certain embodiments, only a single extractive solvent (e.g., DMS or NMP) is present in a composition comprising a volatile anesthetic. In other embodiments, 2, 3, 4, or more extractive solvents may be present in a composition comprising a volatile anesthetic. In certain embodiments, only a single volatile anesthetic (e.g., isoflurane) is present in a volatile anesthetic composition of the present invention; in other embodiments, 2, 3, 4 or more volatile anesthetics may be present in a volatile anesthetic composition of the present invention.

N-methyl pyrrolidone

N-methyl-2-pyrrolidone (NMP) is a solvent which may be included in the volatile anesthetic compositions according to the present invention. NMP is a chemical compound with 5-membered lactam structure. It is a clear to slightly yellow liquid miscible with water and solvents including ethyl acetate, chloroform, benzene and lower alcohols or ketones. NMP is also referred to by the chemical names 1-methyl-2-pyrrolidone or N-methyl-2-pyrrolidinone and m-pyrrole. NMP belongs to the class of dipolar aprotic solvents which also includes dimethylformamide, dimethylacetamide and dimethyl sulfoxide. Due to its good solvency properties, NMP has been used to dissolve a wide range of chemicals, particularly in the polymers field. It also used as a solvent for surface treatment of textiles, resins and metal coated plastics or as a paint stripper.

NMP has been used in the medical industry to improve the solubility of poorly soluble drugs in certain pharmaceutical formulations. For example, NMP has been used with various drugs in veterinary medicine. Several patents have been issued, claiming improvements in drug solubility by the use of NMP, as well as its applicability in topical and transdermal pharmaceutical products for humans.

The relatively non-toxic properties of NMP make it particularly suitable for use as a solvent with the present invention. NMP has a favorable toxicity profile making it a suitable candidate for use in a variety of topical, transdermal and parenteral dosage forms. NMP is available in GMP grade under the trademark Pharmasolve N-methyl-2-pyrrolidone sold by International Specialty Products (ISP; New Jersey, USA).

DMSO

Dimethyl sulfoxide (DMSO) is used in certain embodiments of the present invention as a solvent. DMSO has the formula $(CH_3)_2SO$. DMSO is a polar aprotic solvent that dissolves both polar and nonpolar compounds and is miscible in a wide range of organic solvents as well as water.

DMSO is a relatively non-toxic compound, which makes it particularly suitable for use as a solvent with the present invention. The relative lack of toxicity of DMSO is well established, and the potential use of DMSO for medical purposes was established Stanley Jacob at the University of Oregon Medical School team, who discovered DMSO could penetrate the skin and other membranes without damaging them and could carry other compounds into a biological system. DMSO has also been used as a cryoprotectant and as an anti-inflammatory agent. Dimethyl sulfoxide dissolves a variety of organic substances, including carbohydrates, polymers, peptides, as well as many inorganic salts and gases.

In various embodiments, it is envisioned that lower concentrations, for example, as low as from about 0.1% to about 10%, of DMSO in a composition comprising a volatile anesthetic may be sufficient to eliminate the need for sonication of the composition prior to administration. Higher concentrations, for example, from about 10% to about 75% or higher, of DMSO in a composition comprising a volatile anesthetic may be sufficient to alter the pharmacokinetics of the volatile anesthetic in such a way to allow for an increased duration of analgesic or anesthetic effects.

Volatile Anesthetics

In general, the halogenated ether anesthetics or volatile anesthetics suitable for use with the described compositions and methods include agents which, although often liquid at room temperature, are capable of easily being becoming gaseous or are already gaseous at room temperature and can reduce pain without significant side effects. It may be desirable, for example, to select an agent that is minimally metabolized by the body or is otherwise inert. In this way, liver and kidney toxicity may be minimized. Similarly, it may be desirable for the volatile anesthetic to have a short half-life, or be fast acting to promote titratability (i.e., the subject can easily adjust the delivery amount for the amount of pain he or she is experiencing). An active agent gas that does not produce tolerance (unlike opioids) or dependence (like opioids) may also be desirable.

Volatile anesthetics useful in the compositions and methods of the invention include halogenated ether compounds, isoflurane, sevoflurane, halothane, enflurane, desflurane, methoxyflurane, and diethyl ethers. In certain embodiments xenon may also be used with the present invention. A single agent or mixtures of agents may be particularly suitable for use with the methods described herein.

In various embodiments, a gaseous volatile anesthetic may be used with the present invention. For example, the gaseous volatile anesthetic may be dissolved in a solution according to the present invention and administered in a regional or local anesthesia procedure, such as transdermally, topically, mucosally, buccally, rectally, vaginally, intramuscularly, subcutaneously, epidurally, intrathecally, or in a nerve block procedure. Gaseous volatile anesthetics other than halogenated anesthetics are contemplated, and examples include xenon, nitrous oxide, cyclopropane, and ether, all of which can be used, in various embodiments, in racemic mixture form, or in d-isomer or l-isomer forms. In various embodiments, other biologically active gases (for example, nitric oxide, etc.) may be delivered in a solution to a subject according to the present invention.

More than one volatile anesthetic may be administered at one time, and different volatile anesthetics may be administered at various times throughout a single treatment cycle. For example, 2, 3, 4 or more volatile anesthetics may be simultaneously or repeatedly administered to a subject. When compounds are repeatedly administered to a subject, the duration between administration of compounds may be about 1-60 seconds, 1-60 minutes, 1-24 hours, 1-7 days, 1-6 weeks or more, or any range derivable therein. In some instances, it may be desirable to stage the delivery of different volatile anesthetics depending on their physical and physiological properties. In certain clinical scenarios, a shorter acting agent may be desirable to treat acute pain, whereas a longer lasting agent may be more suited to chronic pain applications.

In certain embodiments, a volatile anesthetic of the present invention is a component of an emulsion, such as a water-in-oil or an oil-in-water emulsion, including, but not limited to a lipid emulsion, such as a soybean oil emulsion. For example, a composition comprising a volatile anesthetic dissolved in a solution comprising an extractive solvent may also comprise a lipid emulsion or an oil-in-water emulsion. In various embodiments, the emulsion of the invention may contain an aqueous solution comprising a volatile anesthetic dissolved in a solution, which may further comprise an extractive solvent. Inclusion of a water-in-oil or an oil-in-water emulsion, such as, for example, a lipid emulsion, in an volatile anesthetic composition may be used, for example, to favorably affect the stability of the volatile anesthetic composition and/or alter the pharmacokinetics of the volatile anesthetic. For example, lipid compositions, lipid emulsions, water-in-oil emulsions, and/or oil-in-water emulsions may be useful for the intrathecal, epidural, transdermal, topical, mucosal, buccal, rectal, vaginal, intramuscular, or subcutaneous delivery of the volatile anesthetic compositions of the present invention. Certain emulsions of isoflurane have been prepared previously for intravenous (da Sila Telles Mathias L, et al., 2004, *Rev. Bras. Anaestesiol Campianas* 54(5), 2004) or epidural administration (Chai et al. 2008, *British J Anesthesia* 100:109-115; Chai et al. Anesthesiology 105: A743, 2006), both for inducing anesthesia.

In certain embodiments, the emulsion of the invention comprises a volatile anesthetic and water, and may further comprise an emulsifier. Emulsions of the invention also include, but are not limited to, nanoemulsions, which are emulsions with a mean droplet size less than those of emulsions. Nanoemulsions are sometimes referred to as microemulsions and submicroemulsions. Often, the physical appearance of a nanoemulsion is transparent, rather than the often milky appearance of an emulsion, due to the reduced mean droplet size.

Emulsions

As would be understood by one of skill, an emulsion consists of a mixture of two or more immiscible liquids (i.e., contains multiple phases) and emulsions are distinct from solutions, which contain one or essentially only one phase. One of the liquids (the dispersed phase) is dispersed in the other (the continuous phase). In one type of emulsion, a continuous liquid phase surrounds droplets of water (for example, a water-in-oil emulsion). In another type of emulsion, oil is dispersed within a continuous water phase (for example, an oil-in-water emulsion). Similarly, emulsification is the process by which emulsions are prepared.

In certain embodiments, a volatile anesthetic of the present invention is a component of an emulsion, such as a water-in-oil or an oil-in-water emulsion, including, but not limited to a lipid emulsion, such as a soybean oil emulsion. For example, a composition comprising a volatile anesthetic dissolved in a solution comprising an extractive solvent may also comprise a lipid emulsion or an oil-in-water emulsion. In various embodiments, the emulsion of the invention may contain an aqueous solution comprising a volatile anesthetic dissolved in a solution, which may further comprise an extractive solvent. Inclusion of a water-in-oil or an oil-in-water emulsion, such as, for example, a lipid emulsion, in an volatile anesthetic composition may be used, for example, to favorably affect the stability of the volatile anesthetic composition and/or alter the pharmacokinetics of the volatile anesthetic. For example, lipid compositions, lipid emulsions, water-in-oil emulsions, and/or oil-in-water emulsions may be useful for the intrathecal, epidural, transdermal, topical, mucosal, buccal, rectal, vaginal, intramuscular, or subcutaneous delivery of the volatile anesthetic compositions of the present invention. Certain emulsions of isoflurane have been prepared previously for intravenous (da Sila Telles Mathias L, et al., 2004, *Rev. Bras. Anaestesiol Campianas* 54(5), 2004) or epidural administration (Chai et al. 2008, *British J Anesthesia* 100:109-115; Chai et al. Anesthesiology 105: A743, 2006), both for inducing anesthesia.

In certain embodiments, the emulsion of the invention comprises a volatile anesthetic and water, and may further comprise an emulsifier. Emulsions of the invention also include, but are not limited to, nanoemulsions, which are emulsions with a mean droplet size less than those of emulsions. Nanoemulsions are sometimes referred to as microemulsions and submicroemulsions. Often, the physical appearance of a nanoemulsion is transparent, rather than the often milky appearance of an emulsion, due to the reduced mean droplet size.

In certain embodiments, the emulsion of the invention can have a lipid component. In various embodiments, the lipid component can comprise an amount ranging from about 1% to 99%, from about 5% to about 75%, from about 10% to about 60%, from about 20% to about 50%, or from about 30% to about 40%, v/v of the emulsion. In various embodiments, the lipid component of the emulsion can be soybean oil, long chain triglyceride, castor oil, corn oil, cottonseed oil, olive oil, peanut oil, peppermint oil, safflower oil, sesame oil, soybean oil, hydrogenated soybean oil, hydrogenated vegetable oil, medium chain triglycerides coconut oil, palm see oil and derivatives, medium chain (C8/C10) mono- and diglycerides, d-alpha-tocopherol, soy fatty acids, or combinations thereof. In certain embodiments, the lipid component of the emulsion is soybean oil. Commercially available lipid compositions that may be useful for the production of the volatile anesthetic compositions of the present invention include, but are not limited to, Intralipid®, Liposyn®, and Nutrilipid®.

In other embodiments, the emulsion further comprises an emulsifier. An emulsifier is a substance which stabilizes an emulsion. An emulsifier may also known as an emulgent. An emulsifier may also be a surfactant. In various embodiments, the emulsifier can be egg phospholipid, purified egg phospholipids, Polyoxyl 35 castor oil (Cremophor EL), Polyoxyl 40 hydrogenated castor oil (Cremophor RH 40), Polyoxyl 60 hydrogenated castor oil (Cremophor RH 60), Polysorbate 20, Polysorbate 80, d-alpha-tocopheryl polyethylene glycol 1000 succinate, Solutol HS-15, propylene glycol or combinations thereof. Various concentrations of an emulsifier may be used with the present invention. For example, a composition of the present invention comprising a volatile anesthetic may comprise about 0.1%-99%, 0.1%-60%, 5%-50%, 10%-40%, 5%-25%, 10%-30%, 10%-25%, 25%-50%, 10%-75%, 25%-75%, 10%-65%, 25%-65%, 10%-60%, 25%-60%, 0.1%, 1%, 5%, 10%, 20%, 25%, 30%, 35%, 40%, 45%, 50%, 55%, 60%, 65%, 70%, 75%, 80% or any range derivable therein, of an emulsifier.

In other embodiments, the emulsion of the invention has a perfluorocarbon component. In various embodiments, the perfluorocarbon component can comprise an amount ranging from about 0.1% to 99%, from about 5% to about 75%, from about 10% to about 60%, from about 20% to about 50%, or from about 30% to about 40%, v/v of the emulsion. In various embodiments, perfluorocarbon may provide additional advantages due to its limited toxicity and ability to scavenge a large amount of gas. In one embodiment, the emulsion of the invention comprises a volatile anesthetic, a perfluorocarbon, water and an emulsifier. A perfluorocarbon, specifically perfluoro-n-octane, has been used clinically, in cases of retinal detachment, by its instillation into the eye in place of the aqueous humor (see Chang, 1992, S. Intl Ophthalmol Clinic 32:153-163).

Liposomes and Microdroplets

In various embodiments, the volatile anesthetics of the present invention can be a component of a liposome suspension. A liposome (for example, multilamellar, unilamellar, and/or multivesicular liposomes) is a microscopic, spherical, fluid-filled structure, with walls comprising one or more layers of phospholipids and molecules similar in physical and/or chemical properties to those that make up mammalian cell membranes. By way of nonlimiting examples, liposomes can be formed from a variety of natural membrane components, such as cholesterol, stearylamine, or phosphatidylcholine (see, for example, U.S. Pat. Nos. 5,120,561 and 6,007,838, each of which is incorporated herein by reference in its entirety), or of pure surfactant components like DOPE (dioleoylphosphatidylethanolamine). Liposomes can be formulated to incorporate a wide range of materials as a payload either in the aqueous or in the lipid compartments or in both. Generally, lipophilic active substances dissolve in the bilayer, amphiphilic substances become associated with the phospholipid membrane and hydrophilic substances occur in solution in the enclosed aqueous volume (Altmann et al., 1990, Drug Res. 40 (II) Nr. 12 pp. 1363-1365; incorporated herein by reference in its entirety).

Liposomes useful as drug carriers or for topical use that are non-toxic and available in industry (Gehring et al., 1990, Drug Res. 40 (II) Nr. 12, pp. 1368-1371; incorporated herein by reference in its entirety). Liposomes have been used as carriers for lipophilic drugs like the anti-tumor and the anti-viral derivatives of azidothymidine (AZT) (Kamps, et al., 1996, Biochim. Biophys. Acta. 1278:183-190). Insulin has also been delivered via liposomes (Muramatsu et al., 1999, Drug Dev. Ind. Pharm. 25:1099-1105). For medical uses as drug carriers, the liposomes can also be injected, and when they are modified with lipids, their surfaces become more hydrophilic and hence their ability to persist can be increased. Polyethylene glycol-modified liposomes have been used as carriers for hydrophilic (water-soluble) anticancer drugs like doxorubicin. Liposomal derivatives of mitoxantrone and others are especially effective in treating diseases that affect the phagocytes of the immune system because they tend to accumulate in the phagocytes, which recognize them as foreign invaders (Rentsch et al., 1997, Br. J. Cancer 75:986-992). Liposomes have also been used to carry normal genes into a cell to treat diseases caused by defective genes (Guo et al., 2000, Biosci. Rep. 20:419-432). The versatility of liposomes, due to the variable composition, enables liposomes to be used to deliver vaccines, proteins, nucleotides, plasmids, drugs, cosmetics, or the volatile anesthetics of the invention to the body.

Liposome compositions of the invention can comprise any range of liposome and volatile anesthetic components, according to the methods and detailed description set forth herein. By way of a non-limiting example, a liposome component of a composition of the invention may include from 0.1% to 99.9% liposome component, or more preferably, from 0.1%-50% liposome component, and even more preferably, from 0.1%-30% liposome component. In various embodiments, the liposome of the invention comprises cholesterol, stearylamine, phosphatidylcholine, dioleoylphosphatidylethanolamine, or combinations thereof.

In various embodiments, the volatile anesthetics of the present invention can also be a component of a microdroplet. A microdroplet of the invention consists of a sphere of organic liquid phase drug that ranges in diameter from about 200 Angstroms to about 10,000 Angstroms that is covered by a monolayer of a suitable lipid. Preferred lipids are phospholipids, which are natural constituents of biological membranes and as such are biologically compatible. Compounds useful for preparing microdroplets include phosphatidylcholine (lecithin), sphingomyelin, phosphatidic acid, phosphatidyl serine, phosphatidyl inositol, diphosphatidyl glycerol and phosphatidyl glycerol.

Microdroplets can be prepared by sonication, including probe or bath sonication, homogenization, microfluidization or by high intensity mechanical agitation. The preferred method of preparing the microdroplets of the invention is by sonication with a probe sonicator. Alternatively, microdroplets can be prepared in a bath sonicator. For small scale preparations a 1.0 cm diameter test tube is suspended, with use of a test-tube clamp, in a bath sonicator filled with water. The components of the microdroplet are first grossly mixed by shaking, Vortex mixing, Polytron or other methods. The suspension is then introduced into the bath sonicator and sonicated for 1-2 hours. If the preparation is to be done on a large scale, it is possible to omit the test tube and introduce the components of the microdroplet directly into a bath sonicator. Microdroplets can also be produced by high intensity mechanical agitation. Useful methods include a Waring blender, a Polytron and high frequency shakers such as a commercial paint shaker. Other materials and methods useful in the preparation of microdroplets are known in the art and are described in U.S. Pat. No. 4,622,219, U.S. Pat. No. 4,725,442, U.S. Pat. No. 5,091,188, Haynes et al. (1989, J Controlled Release 9:1-12) and Haynes et al. (1985, Anesthesiology 63:490-499), all of which references are incorporated herein in their entirety.

Dosing

The amount of the volatile anesthetic to be administered, for example, intrathecally or epidurally, depends on the particular indication desired. For example, the dose will depend on the type of pain intended to be treated. The dose may be different, for instance, if the delivery of the volatile anesthetic is intended to reduce chronic pain as opposed to acute pain. Similarly, the dose may be different if the volatile anesthetic composition will be used to anesthetize a subject (generally or locally, including intrathecally, epidurally, transdermally, topically, mucosally, buccally, rectally, vaginally, intramuscularly, subcutaneously, by local skin infiltration, or in a nerve block procedure). The subject's physical characteristics may also be important in determining the appropriate dosage. Characteristics such as weight, age, and the like may be important factors. For example, the volatile anesthetic may have increased potency with age, as has been demonstrated in the case of the volatile anesthetic isoflurane.

The temperature of the volatile anesthetic may also be considered as a factor in selecting an appropriate dose, as the solubility of many volatile anesthetics may be affected by the temperature of the volatile anesthetic and/or aqueous solution. For example, increases in temperature may increase the solubility, and thus potency, of the volatile anesthetic composition; this property has been demonstrated with certain volatile anesthetics. The particular dosage may also be dependent on the dosing regime chosen. For example, the volatile anesthetic composition may be delivered continuously or periodically. Conversely, the volatile anesthetic composition may be administered as a single administration as a one-time event.

Volatile anesthetics (for example, halogenated anesthetic compounds) may be infused in amounts leading to spinal fluid levels in the range of about 250 to about 50,000 nanograms/ml, depending on the volatile anesthetic selected and the desired effect. In certain embodiments, a volatile anesthetic may be administered to achieve cerebrospinal fluid (CSF) concentration of from about 5 to about 500,000 nanograms/ml. While the dose range will vary depending on the compound selected and patient variability, it is generally true that lower doses such as from about 0.01 to about 10,000 nanogram/ml are more suitable for treating minor to moderate pain, while higher doses such as from about 10,000 nanogram/ml to about 500,000 nanogram/ml or more are suitable for treating severe pain and inducing anesthesia. Of course, the doses may be given once (for example, for a minor single occurrence of pain), repeatedly (for example, for moderate or chronic pain), or continuously (for example, for severe pain or anesthesia purposes). Combinations of these dosing regimes may also be used. For example, a subject suffering from severe pain may require continuous dosing with periodic additional dosing needed for breakthrough pain.

In embodiments where a volatile anesthetic (for example, a volatile anesthetic, such as isoflurane, etc.) is mixed in a solution, such as water, saline or an artificial CSF solution, the concentration of the volatile anesthetic may vary. For example, a solution may contain volatile anesthetic in a v/v ratio of from about 1 to about 99%, from about 10 to about 75%, from about 10 to about 50%, from about 20 to about 50%, from 30 to about 50%, from about 1 to about 45%, from about 1 to about 40%, from about 1 to about 35%, from about 1 to about 30%, from about 1 to about 25%, from about 1 to about 20%, from about 1 to about 15%, from about 1 to about 10%, from about 1 to about 5%, from about 0.5 to about 5%, from about 0.1 to about 5%, from about 0.1 to about 2.5%, from about 0.5 to about 2.5%, or any range derivable therein. In these embodiments, the volatile anesthetic may be, for example, isoflurane, and the solution may be water, a saline solution or an artificial cerebrospinal fluid (ACSF) solution.

The dosing and manner of delivery of the compositions of the invention may be adjusted to achieve pain reduction without substantially interfering with motor function of the subject, for example, by varying the amount, concentration, frequency of administration, and timing of administration.

The volatile anesthetic solution may also contain one or more additives, such as a surfactant, PVP, a polymers, an antimicrobial agent, a preservative etc. In certain embodiments, an volatile anesthetic composition of the present invention may comprise about: 0.1-90% of a volatile anesthetic such as isoflurane, methoxyflurane, or sevofluorane, 0.1-99% of an extractive solvent such as NMP or DMSO, 0.1-99% saline, and 0-50% other additive(s) (for example, glycerol, a surfactant, PVP, etc.). In some embodiments, it may be desirable to produce a concentrated formulation which may be subject to a final dilution prior to administration.

In various embodiments and as shown in the below examples, a solution of about 10% volatile anesthetic, such as isoflurane, may be used; this solution may be administered as a bolus injection, continuously, and/or repeatedly to achieve analgesia and/or anesthesia. Thus, as demonstrated in the below examples, a 10% v/v solution of a volatile anesthetic may be used to induce analgesia. Higher concentrations of volatile anesthetic may be used, in various embodiments, to induce a regional anesthesia.

Methods of Active Agent Delivery

Volatile anesthetics of the present invention may be delivered regionally or locally by a route other than orally, intravenously or by inhalation. "Regional" or "local" anesthesia, as used herein, is distinct from general anesthesia and refers to anesthetic procedures which allow for the preferential delivery of an volatile anesthetic to a specific region of the body, such as near a nerve or a nerve bundle. In contrast, general anesthesia allows for the systemic administration of a volatile anesthetic, for example, via intravenous administration. Regional or local anesthesia typically allows for a lower total body concentration (although elevated local concentrations) of a volatile anesthetic to be administered to a subject for analgesia or diminished pain perception of at least a portion of the subject's body. For example, intrathecal anesthesia, epidural anesthesia, nerve blocks, and local skin infiltration are examples of regional or local anesthesia. In some embodiments, specific concentrations of volatile anesthetic which may be used for regional or local anesthesia include from about 100 to about 500,000 nanogram/ml, from about 100 to about 250,000 nanogram/ml, from about 100 to about 100,000 nanogram/ml, from about 100 to about 50,000 nanogram/ml, from about 100 to about 25,000 nanogram/ml, or from about 100 to about 10,000 nanogram/ml. The specific concentration of volatile anesthetic used may vary depending on the desired effect, and in various embodiments the volatile anesthetic composition is titrated for effect: thus the concentration of volatile anesthetic used or achieved in tissues may vary depending on the specific desired result (e.g., regional anesthesia as compared to analgesia) and/or the particular characteristics of the patient such as sensitivity to the anesthetic.

The present invention may be used with various nerve block procedures. Nerve block procedures according to the present invention may be performed with or without ultrasound visualization; for example, an ultrasound machine may be used to visualize the region of the body involved a the nerve block procedure, such as, for example, various nerve bundles in the shoulder, neck, lower back, etc. The inventors envision that the present invention may be used in conjunction with a variety of surgical procedures, including, for example, but not limited to, knee replacement, hip replacement, shoulder replacement, and/or birthing-related procedures.

In certain embodiments, compositions and methods of the present invention may be used for pain management. Pain management is distinct from general anesthesia in that a lower total body concentration of a volatile anesthetic may be administered to a subject to increase analgesia or decrease perception of pain, preferably without rendering the subject unconscious or substantially interfering with motor function. In some embodiments, specific concentrations of volatile anesthetics which may be used for pain management include from about 100 to about 500,000 nanogram/ml, from about 100 to about 250,000 nanogram/ml, from about 100 to about 100,000 nanogram/ml, from about 100 to about 50,000 nanogram/ml, from about 100 to about 25,000 nanogram/ml, or from about 100 to about 10,000 nanogram/ml.

In some embodiments, specific concentrations of volatile anesthetics which may be used for regional or local anesthesia include from about 100 to about 500,000 nanogram/ml, from about 100 to about 250,000 nanogram/ml, from about 100 to about 100,000 nanogram/ml, from about 100 to about 50,000 nanogram/ml, from about 100 to about 25,000 nanogram/ml, or from about 100 to about 10,000 nanogram/ml.

Epidural or intrathecal administration of a volatile anesthetic may be accomplished via techniques known in the art, such as the use of an intrathecal or epidural catheter. The catheter should be placed closer to the nerves critical for the propagation of any pain sensory information which the practitioner desires to inhibit, without damaging the nerves.

Local topical administration to achieve analgesia prior to or during a medical procedure may be accomplished using techniques known in the art. Examples of such medical procedures include, but are not limited to, surgery, venipuncture, injection, peripheral venous cannulation, incision, suturing, or other procedure.

Other routes of administration which are contemplated include: injection, infusion, continuous infusion, localized perfusion bathing target cells directly, via a catheter, via nanoparticle delivery, topical administration (for example, in a carrier vehicle, a topical control release patch, in a wound dressing, a hydrocolloid, a foam, or a hydrogel), intra-articular, intracranial, and/or intratumoral. An appropriate biological carrier or pharmaceutically acceptable excipient may be used. Compounds administered may, in various embodiments, be racemic, isomerically purified, or isomerically pure.

In certain embodiments, volatile anesthetics of the present invention are not administered intravenously. Intravenous administration is often used for general anesthesia (Mathias et al., 2004, Revista Brasileira de Anestesiologia, ISSN 0034-7094) and typically results in the rapid distribution of the volatile anesthetic throughout the body of a subject. Thus, in certain embodiments, intravenous administration is incompatible for use with regional or local anesthesia.

Solutions

After a volatile anesthetic has been selected, it may be dissolved into a solution. The solution may be an aqueous solution, such as water, saline, artificial cerebrospinal fluid, the subject's own cerebrospinal fluid, or the like. In some variations, other solutions may be appropriate.

Various formulations of saline are known in the art and may be used with the present invention. For example, the saline may be lactated Ringer's solution, acetated Ringer's solution, phosphate buffered saline (PBS), Dulbecco's phosphate buffered saline (D-PBS), Tris-buffered saline (TBS), Hank's balanced salt solution (HBSS), or Standard saline citrate (SSC).

The saline solutions of the present invention are, in certain embodiments, "normal saline" (i.e., a solution of about 0.9% w/v of NaCl). Normal saline has a slightly higher degree of osmolality compared to blood; however, in various embodiments, the saline may be isotonic in the body of a subject such as a human patient. Normal saline (NS) is often used frequently in intravenous drips (IVs) for patients who cannot take fluids orally and have developed severe dehydration. In certain embodiments, "half-normal saline" (i.e., about 0.45% NaCl) or "quarter-normal saline" (i.e., about 0.22% NaCl) may be used with the present invention. Optionally, about 5% dextrose or about 4.5 g/dL of glucose may be included in the saline. In various embodiments, one or more salt, buffer, amino acid and/or antimicrobial agent may be included in the saline.

Various artificial cerebrospinal fluid (ACSF) solutions may be used with the present invention. In certain embodiments, the ACSF is a buffered salt solution (pH 7.4) with the following composition (in mM): NaCl, 120; KCl, 3; $NaHCO_3$, 25; $CaCl_2$, 2.5; $MgCl_2$, 0.5; glucose, 12. ACSF can also be obtained from various commercial sources, such as from Harvard Apparatus (Holliston, Mass.).

In various embodiments, a preservative or stabilizer may be included in the composition or solution. For example, the prevention of the action of microorganisms can be brought about by preservatives such as various antibacterial and antifungal agents, including but not limited to parabens (for example, methylparabens, propylparabens), chlorobutanol, phenol, sorbic acid, EDTA, metabisulfite, benzyl alcohol, thimerosal or combinations thereof. Agents which may be included suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the composition is preferably sterile and must be fluid to facilitate easy injectability. Solutions are preferably stable under the conditions of manufacture and storage and must be preserved against the contaminating action of microorganisms, such as bacteria and fungi. Examples of stabilizers which may be included include buffers, amino acids such as glycine and lysine, carbohydrates such as dextrose, mannose, galactose, fructose, lactose, sucrose, maltose, sorbitol, mannitol, etc. Appropriate stabilizers or preservatives may be selected according to the route of administration desired. A particle filter or microbe filter can be used, and may be necessary according to the route of administration desired.

The weight ranges of compounds in the solution may vary. For example, in various embodiments, the composition may comprise about 1-5 wt % volatile anesthetic, about 1-5 wt % preservative/stabilizer, about 1-5 wt % NaCl, and about 85%-97% water. The ratio of volatile anesthetic to water may be varied as needed to achieve the desired effect (pain reduction or analgesia, regional anesthesia, etc.).

The solution and/or composition may also be sterilized prior to administration. Methods for sterilization are well known in the art and include heating, boiling, pressurizing, filtering, exposure to a sanitizing chemical (for example, chlorination followed by dechlorination or removal of chlorine from solution), aeration, autoclaving, and the like.

The active agent gas may be dissolved into the solution in any number of ways. For example, it may be bubbled through the solution, for example, using a vaporizer, or it may be solubilized by agitation or by sonication. In certain embodiments, a volatile anesthetic may be measured in liquid form and directly mixed into a solution. Of course, other suitable methods of dissolving the volatile anesthetic into solution may also be used. After the volatile anesthetic has been solubilized, it may be administered to a subject in need of pain reduction (including pain reduction in the form of anesthesia) epidurally or intrathecally using techniques well known in the art. In certain embodiments, a volatile anesthetic is mixed with a solution in a closed vacuum container, and the combined solutions are then mechanically agitated for 3-5 minutes and held in a thermo-neutral sonicator until use.

In certain embodiments, solutions of the present invention can be a component of an emulsion, such as a water-in-oil or an oil-in-water emulsion, including a lipid emulsion, such as a soybean oil emulsion. In certain embodiments, saline, artificial CSF, or the patients own CSF, alone or as a constituent of an emulsion, may be used for intrathecal or epidural administration of a volatile anesthetic according to the present invention. Certain emulsions of isoflurane have been prepared previously for intravenous (da Sila Telles Mathias L, et al., 2004, *Rev. Bras. Anaestesiol Campianas* 54(5), 2004) or epidural administration (Chai et al. 2008, *British J Anesthesia* 100:109-115).

Pharmaceutical compositions of the present invention comprise an effective amount of one or more volatile anesthetic or biologically active gas or additional agent dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of a pharmaceutical composition that contains at least one volatile anesthetic or biologically active gas in solution or additional active ingredient will be known to those of skill in the art in light of the present disclosure, as exemplified by *Remington: The Science and Practice of Pharmacy*, 20th Edition (2000), which is incorporated herein by reference in its entirety. Moreover, for animal (for example, human) administration, it will be understood that preparations should meet sterility, pyrogenicity, general safety and purity standards as required by FDA Office of Biological Standards.

In various embodiments, the compositions of the present invention further comprise cyclodextrin. Cyclodextrins are a general class of molecules composed of glucose units connected to form a series of oligosaccharide rings. (See Challa et al., 2005, AAPS Pharm Sci Tech 6:E329-E357). In nature, the enzymatic digestion of starch by cyclodextrin glycosyltransferase (CGTase) produces a mixture of cyclodextrins comprised of 6, 7 and 8 anhydroglucose units in the ring structure ($\alpha$-, $\beta$-, and $\gamma$-cyclodextrin, respectively). Commercially, cyclodextrins are also produced from starch, but different, more specific enzymes are used. Cyclodextrins have been employed in formulations to facilitate the delivery of cisapride, chloramphenicol, dexamethasone, dextromethoraphan, diphenhydramine, hydrocortisone, itraconazole, and nitroglycerin. (See Welliver and McDonough, 2007, Sci World J, 7:364-371). In various embodiments, the cyclodextrin of the invention is hydroxypropyl-Beta-cyclodextrin, sulfobutylether-beta-cyclodextrin, alpha-dextrin or combinations thereof. In certain embodiments, cyclodextrin can be used as a solubilizing agent.

In various other embodiments, the compositions of the present invention can comprise human serum albumin purified from plasma, or recombinant human serum albumin. In certain embodiments, human serum albumin can be used as a solubilizing agent. In other embodiments, the compositions of the invention can comprise propylene glycol. In other embodiments, the compositions of the invention can comprise perfluorooctyl bromide. In other embodiments, the compositions of the invention can comprise perfluorocarbon. In certain embodiments, perfluorocarbon can be used as a solubilizing agent.

Definitions

The articles "a" and "an" are used herein to refer to one or to more than one (i.e. to at least one) of the grammatical object of the article. By way of example, "an element" means one element or more than one element.

The terms "inhibiting," "reducing," or "preventing," and variations of these terms, as used herein include any measurable decrease, including complete or substantially complete inhibition.

The term "effective," as that term is used in the specification and/or claims, means adequate to accomplish a desired, expected, or intended result.

The term "extractive solvent," as used herein, refers to a solvent which may interact with a volatile anesthetic in solution to reduce the volatility of the volatile anesthetic without chemically reacting to the volatile anesthetic.

Throughout this application, the term "about" is used to indicate that a value includes the inherent variation of error for the device, the method being employed to determine the value, or the variation that exists among the study subjects.

The term "or," as used herein, means "and/or" unless explicitly indicated to refer to alternatives only or the alternatives are mutually exclusive, although the disclosure supports a definition that refers to only alternatives and "and/or."

As used herein, the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual and partial numbers within that range, for example, 1, 2, 3, 4, 5, 5.5 and 6. This applies regardless of the breadth of the range.

It is contemplated that any embodiment discussed in this specification can be implemented with respect to any method or composition of the invention, and vice versa. Furthermore, compositions of the invention can be used to achieve methods of the invention.

Other objects, features and advantages of the present invention will become apparent from the detailed description herein. It should be understood, however, that the detailed description and the specific examples, while indicating specific embodiments of the invention, are given by way of illustration only, since various changes and modifications within the spirit and scope of the invention will become apparent to those skilled in the art from this detailed description.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Example 1

Intrathecal Administration of Isoflurane and Sevoflurane

This study was designed to evaluate efficacy of direct intrathecal injection of volatile anesthetic in reducing pain and providing analgesia. The study was conducted over a one (1) month period using the volatile anesthetics isoflurane and sevoflurane injected directly intrathecally or dissolved in saline as shown in the studies below. The subject animal used was the rat, since the rat has a well-established model of pain/analgesia testing. In particular, Sprague-Dawley rats weighing over 350 gm were used. The rats were anesthetized with pentobarbital (50 mg/kg), and the anesthetic depth of the animals was determined by corneal reflex and paw withdrawal reflex to a noxious stimulus.

The neck of the rats were shaved and cleaned with disinfectant solutions in order to avoid bacterial contamination during surgery. A midline surgical dissection of the posterior neck muscles was performed to obtain access to the occipito-atlantoid membrane. This membrane was identified and then dissected. A sterile polyethylene catheter was introduced in the subarachnoid space until the lumbar enlargement of the spinal cord (approximately 7-8 cm measured in each animal). The surgical wound was closed, first suturing the neck muscles with 3-0 silk sutures and then closing the skin incision with staples.

After the surgery, the rats were moved to their cages and a radiant lamp was placed over the cages so that the rats would not undergo anesthetic-induced hypothermia. The rats were continuously monitored from the end of the surgery until they were fully awake. Rats showing any motor impairment after surgery were euthanized.

On the fifth day after surgery, those rats without wound infection or motor dysfunction were transported to the pain behavioral lab to enter the intrathecal study with volatile anesthetics. Twelve rats were selected for the study. All these rats had intrathecal catheters. Isoflurane (1-chloro-2,2,2-trifluoroethyl difluoromethyl ether) and sevoflurane (fluoromethyl 2,2,2-trifluoro-1-(trifluoromethyl)ethyl ether) were used as the halogenated ether compounds. Both of these are halogenated volatile anesthetics, with isoflurane manufactured by Baxter and sevoflurane manufactured by Abbott Laboratories. The 12 rats were divided into 3 groups of four rats each for study A and B.

In the first group, 2 microliters of preservative-free normal saline was injected via the intrathecal catheter into each rat. This catheter was then flushed with preservative-free normal saline. Pain behavioral testing on this group was then performed.

In the second group, 2 microliters of isoflurane was injected via the intrathecal catheter into each rat. This catheter was also flushed with preservative-free normal saline. This group was then subjected to pain behavioral testing.

In the third group, 2 microliters of sevoflurane was injected via the intrathecal catheter into each rat. This catheter was also flushed with preservative-free normal saline. This group was then subjected to pain behavioral testing.

A "hotplate" behavioral test was used to evaluate pain perception and analgesia. The pain behavioral testing model used in these studies have been well established by Tony Yaksh. (See, for example Chaplan et al., 1994, J. Neurosci. Methods, 53:55-63; Yaksh et al., 2001, J. Appl. Physiol., 90:2386-2402; Kim and Chung, 1992, Pain, 50:355-363.; Sorkin et al., 2001, Anesthesiology, 95:965-973). This test involves determining how quickly a rat will withdraw its hind paw in response to a noxious stimulus such as a radiant heat source placed directly underneath its paw. This time for withdrawal is known as "thermal withdrawal latency".

Rats were transferred for testing onto a modified Hargreaves apparatus with a heated glass plate maintained at 25° C. (see Hargreaves et al., 1998, Pain, 32:77-88). A focused projection bulb below the plate was aimed at the mid-plantar surface of the paw. A photodiode-activated timer measured the withdrawal latency, and a cutoff time of 25 seconds was used to prevent tissue damage. Thermal withdrawal latency to radiant heat was measured at 5 minutes and 30 minutes after each intrathecal injection. Each paw was tested three times, and the results were averaged. The below data was collected for both the right and left hind paws:

Group 1: Control Group (Normal Saline) Tested at 5 Minutes

| | Test 1 | | Test 2 | | Test 3 | | |
|---|---|---|---|---|---|---|---|
| | Right | Left | Right | Left | Right | Left | Average |
| Rat 1: | 9.00 | 9.26 | 10.45 | 6.74 | 8.42 | 9.95 | 8.97 |
| Rat 2: | 11.23 | 9.32 | 6.34 | 7.98 | 10.65 | 8.73 | 7.19 |
| Rat 3: | 7.83 | 8.21 | 9.67 | 11.90 | 8.55 | 6.38 | 8.76 |
| Rat 4: | 9.72 | 8.04 | 6.77 | 8.92 | 7.88 | 8.95 | 8.38 |
| | | | | | | | Group 1 Average: 8.33 seconds |

Group 2 Study A: Isoflurane Group Tested at 5 Minutes

| | Test 1 | | Test 2 | | Test 3 | | |
|---|---|---|---|---|---|---|---|
| | Right | Left | Right | Left | Right | Left | Average |
| Rat 5: | 19.81 | 17.23 | 20.38 | 18.91 | 20.34 | 18.82 | 19.25 |
| Rat 6: | 17.19 | 19.24 | 15.88 | 17.65 | 18.59 | 20.72 | 18.21 |
| Rat 7: | 19.20 | 18.11 | 17.90 | 19.80 | 16.71 | 20.07 | 18.63 |
| Rat 8: | 20.31 | 19.71 | 18.34 | 17.18 | 16.75 | 16.38 | 17.95 |
| | | | | | | | Group 2 Average: 18.51 second |

Group 3 Study B: Sevoflurane Group Tested at 5 Minutes

| | Test 1 | | Test 2 | | Test 3 | | |
|---|---|---|---|---|---|---|---|
| | Right | Left | Right | Left | Right | Left | Average |
| Rat 9: | 13.81 | 14.90 | 13.23 | 15.11 | 16.03 | 14.83 | 14.65 |
| Rat 10: | 17.19 | 13.38 | 14.29 | 12.31 | 13.75 | 12.01 | 13.82 |
| Rat 11: | 14.98 | 12.34 | 13.93 | 11.03 | 12.37 | 14.16 | 13.14 |
| Rat 12: | 10.31 | 11.83 | 13.20 | 12.66 | 17.59 | 12.31 | 12.98 |
| | | | | | | | Group 3 Average: 13.65 second |

These rats were then allowed time to recover from their intrathecal injection. There were no apparent adverse effects such as respiratory depression, cardiac, or neurological compromise. At 30 minutes after the injection, the rats were tested again, according to grouping:

Group 1: Control Group (Normal Saline) Tested at 30 Minutes

|  | Test 1 | | Test 2 | | Test 3 | | |
| --- | --- | --- | --- | --- | --- | --- | --- |
|  | Right | Left | Right | Left | Right | Left | Average |
| Rat 1: | 7.32 | 8.02 | 9.17 | 8.64 | 5.89 | 7.71 | 7.79 |
| Rat 2: | 6.77 | 5.98 | 7.81 | 6.54 | 9.03 | 8.20 | 8.59 |
| Rat 3: | 7.08 | 8.39 | 7.26 | 8.49 | 9.23 | 9.84 | 8.38 |
| Rat 4: | 8.36 | 9.44 | 9.15 | 9.67 | 8.54 | 7.92 | 8.85 |
|  |  |  |  |  |  |  | Group 1 Average: 8.40 seconds |

Group 2, Study A: Isoflurane Group Tested at 30 Minutes

|  | Test 1 | | Test 2 | | Test 3 | | |
| --- | --- | --- | --- | --- | --- | --- | --- |
|  | Right | Left | Right | Left | Right | Left | Average |
| Rat 5: | 9.87 | 9.12 | 10.59 | 9.02 | 8.54 | 9.77 | 9.48 |
| Rat 6: | 9.08 | 6.35 | 7.81 | 8.22 | 10.49 | 11.62 | 8.93 |
| Rat 7: | 6.32 | 8.37 | 9.48 | 8.45 | 11.03 | 10.48 | 10.52 |
| Rat 8: | 9.41 | 10.27 | 6.76 | 7.04 | 7.88 | 10.32 | 9.21 |
|  |  |  |  |  |  |  | Group 2 Average: 9.53 seconds |

Group 3, Study B: Sevoflurane Group Tested at 30 Minutes

|  | Test 1 | | Test 2 | | Test 3 | | |
| --- | --- | --- | --- | --- | --- | --- | --- |
|  | Right | Left | Right | Left | Right | Left | Average |
| Rat 9: | 9.23 | 8.54 | 7.30 | 8.29 | 9.43 | 8.87 | 8.61 |
| Rat 10: | 7.38 | 6.87 | 8.92 | 7.99 | 10.83 | 8.10 | 8.35 |
| Rat 11: | 10.05 | 8.44 | 9.32 | 11.74 | 7.66 | 6.13 | 8.89 |
| Rat 12: | 9.55 | 10.93 | 8.67 | 6.68 | 9.27 | 12.11 | 9.54 |
|  |  |  |  |  |  |  | Group 3 Average: 8.84 seconds | gases. None of the rats in the study experienced adverse effects, and all of them fully recovered from the intrathecal injection after 30 minutes, as indicated by the return to thermal latency baseline for all groups.

Example 2

Intrathecal Administration of Isoflurane Dissolved in Saline

Isoflurane was dissolved into saline using the following method (also referred to as the "bubbling" method). Study C: A mock vaporizing device was created using a 500 ml modified Erlenmeyer flask (2 inlets and 1 catheter into the liquid phase). The flask was partially filled with 0.9% normal saline and a stoppered glass pipette was inserted into the bottom of the liquid phase for injection of isoflurane. A second egress pipette allowed egress of gas from the closed container. 2% isoflurane solution in oxygen at 2 L/min was injected through the pipette, saturating the 0.9% saline solution after approximately 10 minutes of bubbling. 5 mL was drawn from the saturated saline solution and administered to 10 animals using the procedures outlined in Example I above.

For study C, all animals were prepared as for experiments A and B. The inventors injected 4 animals with 5 microliter of dissolved isoflurane (as prepared in 0030) via intrathecal catheter. Note, control (baseline) latency to paw withdrawal is different in Study C due to a different intensity of heat lamp used. Each animal serves as its own control in study C.

Figure 2:
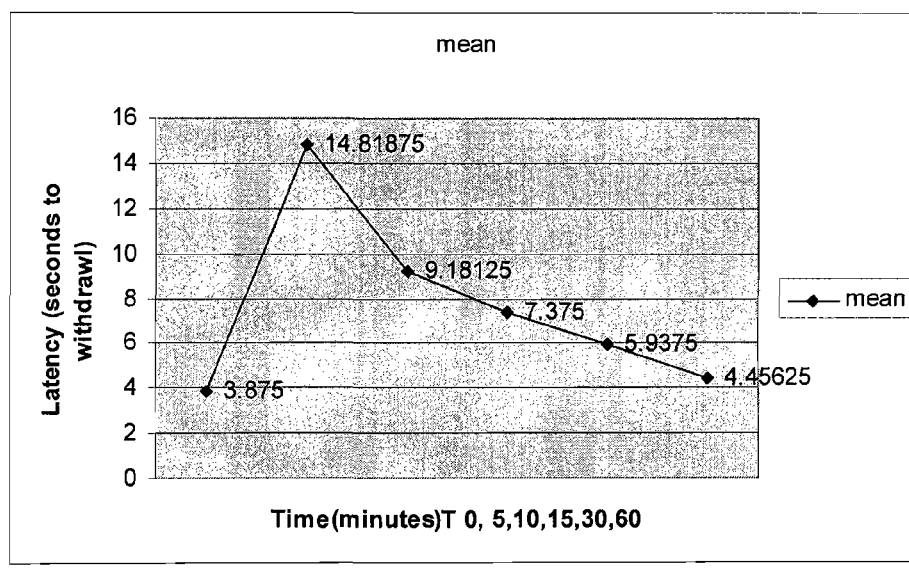
FIG. 2 depicts the results of an example experiment examining the inhibition of pain via intrathecal administration of isoflurane solution as measured using the hotplate test.

Study C Data is presented here: in seconds to paw withdrawal to heat source. Table and graphic format. Results are shown in FIG. 2.

|  | CONTROL | 5 MIN | 10 MIN | 15 MIN | 30 MIN | 60 MIN |
| --- | --- | --- | --- | --- | --- | --- |
| RAT 1 | 4.8 | 11 | 5.4 | 7.6 | 6.8 | 6.1 |
|  | 4.4 | 15 | 9 | 7.3 | 7.2 | 5.8 |
|  | 4.8 | 19.5 | 9 | 8.8 | 4.9 | 5.1 |
|  |  | 20 | 6.8 | 7 | 5.2 | 4.9 |
| RAT 2 | 3.4 | 10.9 | 9.9 | 10.4 | 8.2 | 3.8 |
|  | 4.3 | 12.6 | 8.7 | 9.4 | 6.9 | 4.7 |
|  | 3.6 | 18.1 | 12 | 5.4 | 8.1 | 7 |
|  |  | 17.3 | 9 | 13.4 | 6.4 | 4.1 |
| RAT 3 | 3.6 | 14.2 | 12.2 | 6.1 | 5.2 | 4.2 |
|  | 3.8 | 20 | 12 | 7.1 | 6.1 | 3.5 |
|  | 4.7 | 20 | 9.1 | 4.8 | 5.8 | 3.3 |
|  |  | 16 | 8.9 | 5.2 | 6.5 | 3.8 |
| RAT 5 | 3.9 | 9.8 | 8.8 | 7.9 | 4.9 | 4.2 |
|  | 2.6 | 11.8 | 7.8 | 6.4 | 4.3 | 3.5 |
|  | 2.6 | 9.1 | 10.2 | 6.9 | 4.7 | 3.8 |
|  |  | 11.8 | 8.1 | 4.3 | 3.8 | 3.5 |
| mean | 3.875 | 14.81875 | 9.18125 | 7.375 | 5.9375 | 4.45625 |
| SD | 0.767671 | 3.809235 | 1.77067 | 2.231171 | 1.266331 | 1.073293 |

The results of this study demonstrated the efficacy of intrathecal administration of volatile anesthetics in reducing pain. At the smallest intrathecally delivered dose of 2 microliters, an analgesic effect of isoflurane and sevoflurane was shown. The thermal latency time was significantly increased, thus showing that the thermal C-fiber pain pathway was effectively dampened. This study also shed some light into the safety of intrathecally delivering active agent Example 3

Intrathecal Inhibition of Pain Using Isoflurane Dissolved in Artificial Cerebrospinal Fluid Pain sensitivity was measured after intrathecal administration of isoflurane in artificial cerebrospinal fluid (ACSF). Further, as detailed below, the isoflurane was first dissolved in ACSF and then sonicated before administration. The dose response relationship was then evaluated by generating a stimulus-response (SR) graph in order to determine relevant concentrations of isoflurane that may be administered intrathecally to achieve analgesia or anesthesia. The characterization of the pharmacological profile of intrathecal administration of isoflurane in AC SF was performed in this example using rats; further, as would be appreciated by one of skill in the art, analogous approaches may be used to determine the precise pharmacological profile in humans.

Isoflurane dissolved in ACSF was prepared by the following method. Isoflurane was mixed in a closed vacuum container in a v/v ratio of 10-50% with buffered salt solution that approximates cerebrospinal fluid (pH 7.4) with the following composition (in mM): NaCl, 120; KCl, 3; NaHCO$_3$, 25; CaCl$_2$, 2.5; MgCl$_2$, 0.5; glucose, 12. The combined solutions were mechanically agitated for 3-5 minutes and then held in a thermo-neutral sonicator until use.

Isoflurane in ACSF was then administered to rats intrathecally via the following method. Treatment solution is delivered via intrathecal catheter that overlies lumbar segment L1-2 in a volume of 10 µl followed by a 10 µl flush of ACSF.

Pain perception was tested after intrathecal administration of isoflurane dissolved in artificial CSF using the "hotplate" behavioral test, as described above, with the modification that a cutoff time of 20 seconds was used. As stated above the "hotplate" behavioral test involves testing the hind paw withdrawal latency to radiant heat (i.e., duration of time between before a rat to lifts a paw away from a heat source).

Figure 3:
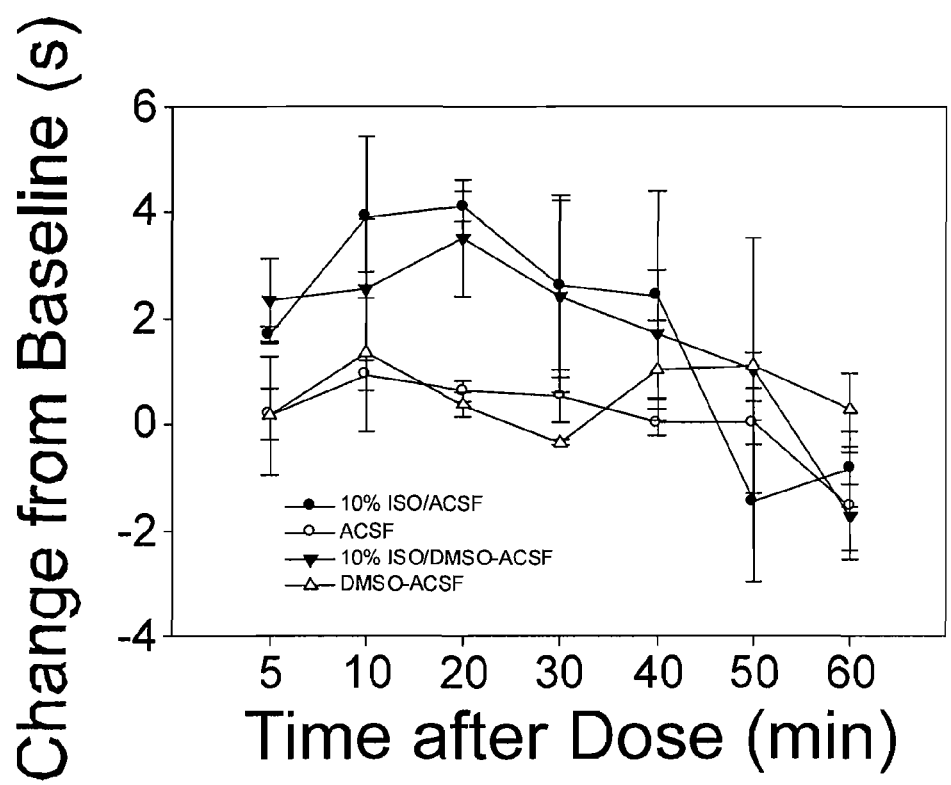
FIG. 3 depicts the results of an example experiment examining the inhibition of pain using intrathecal isoflurane in artificial cerebrospinal fluid (ACSF) and/or DMSO. The time course for Isoflurane-ACSF and Isoflurane-DMSO/ACSF, at a dose of 1.46 mg isoflurane, is shown.

Intrathecal administration of isoflurane in ACSF resulted in analgesia. As shown in FIG. 3, intrathecal administration of isoflurane in ACSF (i.e., at a 1.46 mg dose of isoflurane) resulted in analgesia as measured by testing the hind paw withdrawal threshold to radiant heat. A 10 µL solution of isoflurane in ACSF (10% v/v) was used. As described below, this dose of isoflurane represents a moderate dose of intrathecal isoflurane. Further, as shown in FIG. 3, DMSO may be included in the pharmaceutical composition for intrathecal injection. A concentration of 1% DMSO was used.

Figure 4:
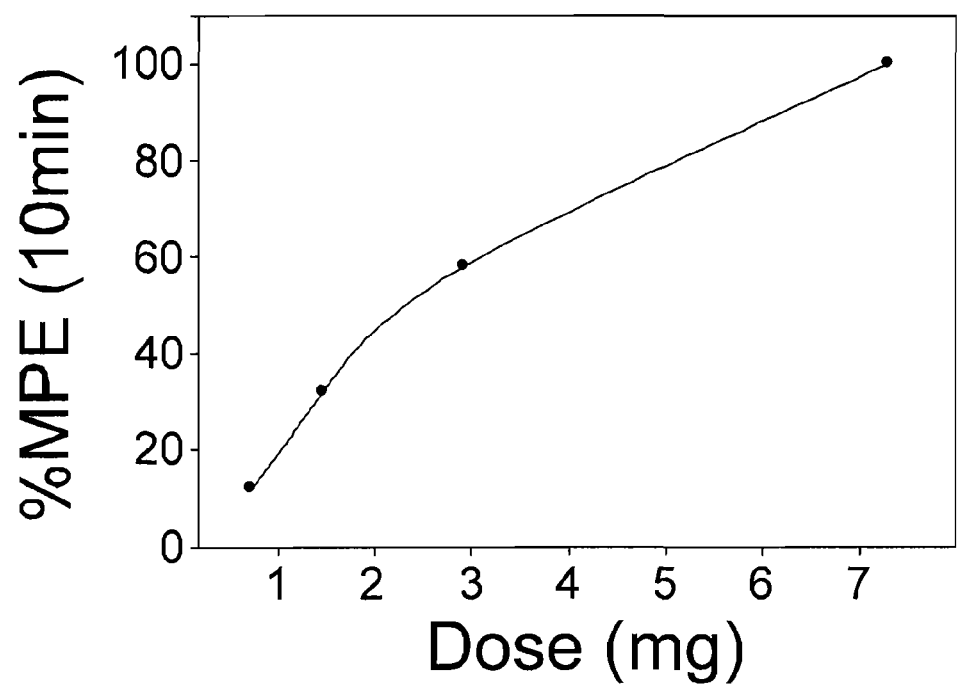
FIG. 4 depicts the results of an example experiment evaluating the stimulus response (SR) of the maximal possible effect (MPE) by dose for the time point of 10 minutes after intrathecal injection of isoflurane-ACSF.

The dose response relationship was then evaluated by generating a stimulus-response (SR) graph in order to standardize responses across animals and determine relevant concentrations of isoflurane that may be administered intrathecally to achieve analgesia or anesthesia. FIG. 4 shows an stimulus-response (SR) graph of the maximal possible effect (MPE) by dose for the time point of 10 minutes after the injection of isoflurane in ACSF. Various doses of isoflurane are shown on the x-axis; for example, the 10% v/v solution of isoflurane used above, as shown in FIG. 3, corresponds to approximately a 34% MPE as shown in FIG. 4. Pharmaceutical compositions including ACSF and/or 1% DMSO are shown in FIG. 3. MPE is used here to standardize responses across animals. MPE is calculated as ((drug response time–baseline response time)/(cutoff time–baseline response time))*100. The cutoff time used here was 20 seconds. As shown in FIG. 4, a substantial analgesic effect was observed. A concentration of 1% DMSO was used.

Example 4

Intraplanar Administration of Isoflurane

Rats are assessed for response to thermal stimulation using the Planar Heat Stimulation Test (i.e., radiant heat) (Planar Analgesia Instrument, Ugo Basile, Italy) by measuring paw withdrawal latency. 100 µl of pureform Isoflurane or 100 µl of 2% Lidocaine was injected subcutaneously into the planar surface of one hindpaw of each rat. For each rat, the untreated, contralateral hindpaw served as its own control.

After the rats acclimated for 15 minutes under acrylic boxes that allow minimal movement, a heat source was positioned beneath the mid-plantar surface of the hind paw. Withdrawal latency was defined as the period of time from the beginning of the thermal stimulation to the brisk withdrawal of the hind paw. To avoid tissue damage, a cutoff time of 22 seconds was set. Thermal stimulation was applied three times to each hind paw at an interstimulus interval of 3-5 minutes. Thermal withdrawal latency was assessed before and after the treatment. An increase in the withdrawal latency in the treated paw compared to the control paw was assessed as analgesic activity of the tested formulation.

Figure 5:
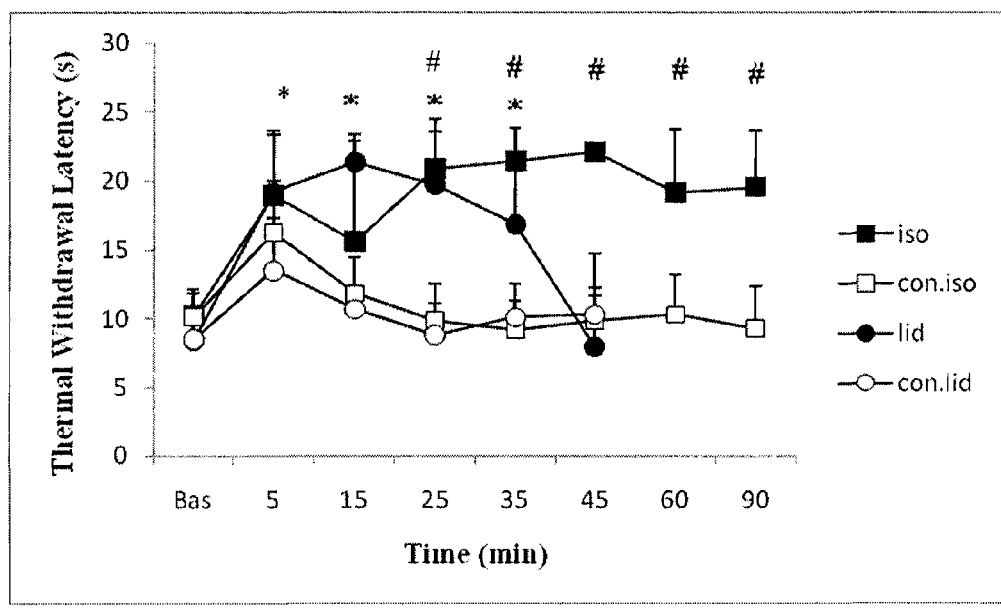
FIG. 5 depicts the results of an example experiment examining the inhibition of pain via subcutaneous administration of isoflurane.

The results of this experiment are shown in FIG. 5. For statistical comparison, student paired t-test analysis was used. Differences were considered significant at P<0.05 (# P<0.05 isoflurane versus control n=4; * P<0.05 lidocaine versus control n=3).

The administration of isoflurane into the hindpaw produced significant antinociceptive effect (iso) when compared to the untreated paw (con.iso). The antinociceptive effect began at 25 minutes after administration and continued throughout the experiment. The administration of lidocaine (lid versus con.lid) resulted in significant antinociceptive effect, which began at 5 minutes after administration, peaked at 15 minutes, and returned to baseline levels at 45 minutes.

Example 5

Isoflurane Stability

In the Examples that follow, the stability of isoflurane in the described compositions was determined in two ways. First, the compositions were examined for the presence of phase separation at the macroscopic level. Secondly, isoflurane content of the compositions was determined by weighing the remaining isoflurane in the composition when they were left uncapped over time. Briefly, glass vials were filled with 5-10 ml of the composition vehicle and then weighed; one of them received only vehicle (i.e., no isoflurane) and served as control. The other vials received varying amounts of isoflurane. They were left uncapped in the hood. Over time, the vials were weighed to see if the isoflurane stayed in the composition or had evaporated. The amount evaporated over time in the vehicle control was subtracted from that in the isoflurane-containing composition.

The pure form of isoflurane is a volatile anesthetic. In order to assess the volatility of isoflurane, two vials received the indicated amounts of pure form isoflurane. The vials were placed in the chemical fume hood and left uncapped. The vials were weighed at the indicated times to determine the amount of evaporated isoflurane. As it is shown in the table below 0.7893 g isoflurane was evaporated within 3 hours, while 3.4825 g isoflurane took approximately 8 hrs to evaporate completely. These amounts of isoflurane are similar to the amounts of isoflurane that were used to prepare the isoflurane compositions in the Examples that follow.

| Pure form of Isoflurane (g) | 0 h (% remaining iso) | 0.25 h (% remaining iso) | 1 h (% remaining iso) | 2 h (% remaining iso) | 3 h (% remaining iso) | 5 h (% remaining iso) | 7 h | 8 h |
|---|---|---|---|---|---|---|---|---|
| 0.7893 | 100 | 85 | 52 | 14 | 0 | | | |
| 3.4825 | 100 | 96 | 86 | 75 | 62 | 38 | 13 | 3 |

Example 6

Preparation of Isoflurane Solution (v/v) with NMP

Pure isoflurane USP (Forane) liquid was mixed with NMP (Sigma-Aldrich) in the indicated concentrations; the mixture was vortexed vigorously to prepare homogenous isoflurane-NMP solution. In order to reduce the amount of NMP in the solution, saline (0.9% NaCl) was added to the mixture.

| | NMP (%) | Saline (%) | Isoflurane (%) | Appearance of solutions |
|---|---|---|---|---|
| 1 | 90 | — | 10 | Clear |
| 2 | 60 | — | 40 | Clear |
| 3 | 63 | 27 | 10 | Clear |
| 4 | 72 | 20 | 8 | Clear |

| Isoflurane concentration in NMP | 0 h (% remaining iso) | 0.25 h (% remaining iso) | 1 h (% remaining iso) | 16 h (% remaining iso) | 24 h (% remaining iso) |
|---|---|---|---|---|---|
| 10 | 100 | 99 | 99 | 94 | 91 |
| 30 | 100 | 99 | 98 | 90 | 86 |

As it is shown in the tables above, 10% and 40% of isoflurane was mixed with NMP, and the resulting solution looked clear. Moreover, the addition of NMP reduced the volatility of isoflurane, as compared with Example 5.

Example 7

Preparation of Emulsified Isoflurane (v/v) in Intralipid

Pure isoflurane USP (Forane) liquid is mixed with Intralipid 20% or 30% (Baxter) at the indicated concentrations; the mixture was vortexed vigorously and sonicated for 30 minutes to prepare homogenous isoflurane-intralipid emulsion.

| | Lipid Emulsion | Isoflurane Concentration | Appearance of Emulsions |
|---|---|---|---|
| 1 | 20% Intralipid | 1-6% | Homogenous |
| 2 | 30% intralipid | 6-10% | Homogenous |

| Isoflurane concentration in intralipid 20% | 0 h (% remaining iso) | 0.25 h (% remaining iso) | 1 h (% remaining iso) | 16 h (% remaining iso) | 24 h (% remaining iso) |
|---|---|---|---|---|---|
| 2 | 100 | 95 | 95 | 92 | 91.7 |
| 3 | 100 | 93 | 92 | 70 | 69.8 |
| 4 | 100 | 94 | 92 | 55 | 55.3 |
| 5 | 100 | 96 | 95 | 60 | 58.9 |

Intralipid emulsions with the indicated amount of isoflurane looked homogenous and uniform. Moreover, intralipid reduced the volatility of isoflurane, as compared with Example 5.

One of skill in the art will realize that emulsions of isoflurane can be made using other lipids, including other emulsion preparations, such as 10% (w/v) Intralipid, using variations of the methods described herein. Other commercially available lipid compositions that may be useful for the production of the volatile anesthetic compositions of the present invention include, but are not limited to, Liposyn® (B. Braun) and Nutrilipid® (B. Braun). One of skill in the art will also realize that emulsions of desflurane, sevoflurane, isoflurane, enflurane, methoxyflurane and halothane can be produced using variations of the methods described herein.

Example 8

Preparation of Emulsified Isoflurane (v/v) in Intralipid and NMP

Pure isoflurane USP (Forane) liquid is mixed with NMP (Sigma-Aldrich) in the indicated concentrations; the NMP-Isoflurane solution was added to intralipid 20% or 30% (Baxter). The mixture was vortexed vigorously and sonicated for 30 minutes to prepare homogenous isoflurane-NMP-intralipid emulsion.

| | 20% Intralipid (%) | NMP (%) | Isoflurane (%) | Appearance of emulsions |
|---|---|---|---|---|
| 1 | 75 | 15 | 10 | Homogenous |
| 2 | 80 | 10 | 10 | Homogenous |

| Vehicle | Isoflurane (%) | 0 h (% remaining iso) | 0.25 h (% remaining iso) | 1 h (% remaining iso) | 16 h (% remaining iso) | 24 h (% remaining iso) |
|---|---|---|---|---|---|---|
| 20% intralipid + 15% NMP | 5 | 100 | 98 | 94 | 88 | 85 |
| 20% intralipid + 15% NMP | 10 | 100 | 98 | 97 | 93 | 89 |

Intralipid emulsions with the indicated amount of isoflurane in the presence of NMP looked homogenous and uniform. In the presence of NMP, intralipid was able to hold more isoflurane than in the absence of NMP, as compared with Example 7. In addition, the combination of intralipid and NMP reduced the volatility of isoflurane, as compared with Example 5.

One of skill in the art will realize that emulsions of isoflurane can be made using other lipids, including other emulsion preparations, such as 10% (w/v) intralipid, using variations of the methods described herein. Other commercially available lipid compositions that may be useful for the production of the volatile anesthetic compositions of the present invention include, but are not limited to, Liposyn® (B. Braun) and Nutrilipid® (B. Braun). One of skill in the art will also realize that emulsions of desflurane, sevoflurane, isoflurane, enflurane, methoxyflurane and halothane can be produced using variations of the methods described herein.

Example 9

Preparation of Polysorbate 80 (Tween 80)-Based Emulsified Isoflurane

Isoflurane was added to Tween 80 (3% v/v) for a total volume of 10 ml. The mixture was vortexed vigorously and sonicated for 30 minutes to prepare homogenous isoflurane emulsion. In some cases, 1,2-dimyristoyl-sn-glycero-3-phosphocholine (DMPC) was included in the formulation. First, DMPC (0.3% or 0.6%) was dissolved in Tween 80 (3% v/v), then isoflurane was added to the Tween-DMPC mixture, which was followed by 30 minutes of sonication.

| | 3% Tween 80 (%) | DMPC (%) | Isoflurane (%) | Appearance of emulsions |
|---|---|---|---|---|
| 1 | 95 | — | 5 | Homogenous |
| 2 | 93 | 0.3 | 7 | Homogenous |
| 3 | 93 | 0.6 | 7 | Homogenous |

| Vehicle | Isoflurane (%) | 0 h (% remaining iso) | 0.25 h (% remaining iso) | 1 h (% remaining iso) | 16 h (% remaining iso) | 24 h (% remaining iso) |
|---|---|---|---|---|---|---|
| 3% Tween | 7 | 100 | 97 | 95 | 91 | 85 |
| 3% Tween + 0.3% DMPC | 7 | 100 | 98 | 96 | 94 | 89 |
| 3% Tween + 0.6% DMPC | 7 | 100 | 100 | 100 | 99 | 94 |

Tween 80-based emulsions appeared homogenous. When DMPC was added, the same amount of Tween 80 was able to hold more isoflurane than without DMPC. Moreover, the combination of isoflurane with Tween 80 or Tween 80 DMPC reduced the volatility of isoflurane, as compared with Example 5.

Example 10

Preparation of Isoflurane Solution (v/v) with Propylene Glycol

Pure isoflurane USP (Forane) liquid was mixed with Propylene Glycol (Sigma-Aldrich) at the indicated concentrations; the mixture was vortexed vigorously to prepare homogenous isoflurane-Propylene Glycol solution.

| | Propylene Glycol (%) | Saline (%) | Isoflurane (%) | Appearance of solutions |
|---|---|---|---|---|
| 1 | 90 | — | 10 | Clear |
| 2 | 70 | — | 30 | Clear |
| 3 | 72 | 20 | 8 | Clear |

| Isoflurane concentration in Propylene Glycol | 0 h (% remaining iso) | 0.25 h (% remaining iso) | 1 h (% remaining iso) | 16 h (% remaining iso) | 24 h (% remaining iso) |
|---|---|---|---|---|---|
| 10 | 100 | 89 | 86 | 44 | 23 |
| 30 | 100 | 94 | 90 | 53 | 35 |

Eight percent, 10% and 30% of isoflurane was mixed with propylene glycol, and the resulting solutions appeared clear. Moreover, propylene glycol reduced the volatility of isoflurane, as compared with Example 5.

Example 11

Preparation of Cremophor EL-Based Emulsified Isoflurane

Isoflurane was added to an aqueous solution of Cremophor EL (10% v/v) for a total volume of 10 ml. The mixture was vortexed vigorously and sonicated for 30 minutes to prepare homogenous isoflurane emulsion.

| | 10% Cremophor EL (%) | Isoflurane (%) | Appearance of the emulsion |
|---|---|---|---|
| 1 | 95 | 5 | Milky |
| 2 | 90 | 10 | Milky |

| Vehicle | Isoflurane Concentration | 0 h (% remaining iso) | 0.25 h (% remaining iso) | 1 h (% remaining iso) | 16 h (% remaining iso) | 24 h (% remaining iso) |
|---|---|---|---|---|---|---|
| 10% Cremophor | 5 | 100 | 90 | 85 | 68 | 54 |
| 10% Cremophor | 10 | 100 | 91 | 87 | 73 | 60 |

Cremophor EL-based emulsions with the indicated amount of isoflurane appeared milky. Moreover, the Cremophor EL-based emulsions reduced the volatility of isoflurane, as compared with Example 5.

Example 12

Preparation of Isoflurane Solution (v/v) with Dimethyl Sulfoxide (DMSO)

Pure isoflurane USP (Forane) liquid was mixed with DMSO (BDH) at the indicated concentrations. The mixture was vortexed vigorously to prepare homogenous isoflurane-DMSO solution. The isoflurane solutions containing DMSO appeared clear.

| | DMSO (%) | Saline (%) | Isoflurane (%) | Appearance of solutions |
|---|---|---|---|---|
| 1 | 90 | — | 10 | Clear |
| 2 | 50 | — | 50 | Clear |
| 3 | 72 | 20 | 8 | Clear |

Example 13

Preparation of Isoflurane Solution (v/v) in Perfluorooctyl Bromide

Pure isoflurane USP (Forane) liquid was mixed with Perfluorooctyl Bromide (Acros Organics) at the indicated concentrations. The mixture was vortexed vigorously to prepare homogenous isoflurane-Perfluorooctyl Bromide solution. The isoflurane solutions containing Perfluorooctyl Bromide appeared clear.

| | Perfluorooctyl Bromide (%) | Isoflurane (%) | Appearance of solutions |
|---|---|---|---|
| 1 | 90 | 10 | Clear |
| 2 | 80 | 20 | Clear |

Example 14

Topical Application of Isoflurane for Analgesia

To evaluate the efficacy of topical isoflurane, a small amount of (1 cc) of 50% ISO/DMSO solution was applied to the skin of a human subject. The subject observed local anesthetic properties where the 50% ISO/DMSO solution was applied, with a notable local anesthetic response to light touch for approximately one hour duration. No skin irritation was observed.

To further quantify this local anesthetic response in human subjects, clinical studies assessing any of the volatile anesthetic compositions described herein, may be performed as described below. Isoflurane (ISO) is a widely used volatile anesthetic agent with a well established safety profile. Dimethyl sulfoxide (DMSO) is an organic solvent which has been used as a drug delivery system to facilitate drug movement across the stratum corneum (the water impermeable skin layer). Previous work had shown local anesthesia with lecithin-coated microdroplets of methoxyflurane (Haynes and Kirkpatrick, 1991, Reg Anesth 16:173-80).

The following approach may be used to test the analgesia of any of the volatile anesthetic compositions described herein. Studies similar to those involving topical amitryptiline studies (see clinicaltrials.gov/show/NCT00471445) may be performed. Cutaneous evaluation in human volunteers for efficacy and or local skin irritation may also be tested. In the example of amitryptiline, important advances came through pilot human trials with volunteers comparing different doses and vehicle alone for skin irritation and pain blocking properties (Gerner et al., 2003, Reg Anesth Pain Med. 28:289-93). To differentiate between vehicle and active drug, several sites will be tested as outlined below to include a vehicle only site versus drug+vehicle (in different doses).

Subject Eligibility: Test subjects should be volunteer adults without health problems including lack of skin sensitivity or other medical problems. They need to be literate and agree to an application of test medications to their forearm with a subsequent testing protocol for 4 hours.

Treatment Plan: Healthy volunteers may have 3 circles approximately 10 cm in diameter drawn on their nondominant forearm with a marking pen. Baseline vital signs may be taken.

Medication may be applied as follows: Low dose volatile anesthetic composition, High dose volatile anesthetic composition, and Vehicle alone, each to one of the three spots respectively, and covered with a tegaderm (6×7 cm, 3M Healthcare, St Paul Minn.). This may be removed after 15 minutes.

Testing may be done at the center of the three circles at baseline (pre-application), 15 minutes (after dressing removal), 60 minutes, 3 hours, and 24 hours. Testing may include sensitivity to light touch with:

Touch detection thresholds. (A delta-small myelinated fibers-"fast pain" touch): Touch detection thresholds may be determined using the up/down method of Dixon 1 with 6 von Frey monofilaments that are calibrated to administer a force of 0.1, 0.5, 0.9, 3.2, 6.1 or 8.0 mN. Starting with 0.5 mN, the von Frey monofilament may be applied for approximately 1 sec. If the subject fails to detect the stimulus, then the next higher force von Frey monofilament is applied. When the subject detects the presence of the stimulus, the next lower von Frey is administered. The up/down test sequence continues for four additional von Frey applications after the initial detection. The 50% mechanical detection threshold is calculated using the procedure described in Dixon 1. If there is no detection to the highest force von Frey monofilament, then the 50% detection threshold is assigned the value of 19 mN.

Pain Detection (C Fiber-large unmyelinated "slow pain"), Sharpness threshold and pain to needle probes: Sharpness detection may be determined using a weighted needle device 2. The tip of 30 gauge needle (200 im diameter) is filed to produce a flat, cylindrical end. A cotton tip applicator is inserted into the Luer connection of the needle, and washers are placed on the shaft of the cotton tip applicator to achieve the desired force level for the stimulus. The entire assembly is then placed inside a 30 cc syringe so that the needle came out of the tip of the syringe and the assembly moved freely within the syringe. When the needle is applied to the skin surface, a reliable and consistent force is applied. Three forces will be used: 100, 200 and 400 mN. Each stimulus is applied for about 1 second. Each force is applied 10 times within each area of interest in a pseudorandom order. The subjects are instructed to indicate if the stimulus is sharp. If a stimulus is sharp, the subject then indicates if the stimulus is painful.

To assess for skin irritation, the subjects may be asked to rate the "local skin irritation" at each location at each time point on a 0-10 scale (0=not irritated at all and 10=extremely irritated). Finally, the skin may be examined for redness and obvious irritation at the site at each time point as a "present or absent."

The disclosures of each and every patent, patent application, and publication cited herein are hereby incorporated herein by reference in their entirety.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of reducing pain in a subject in need thereof, the method comprising topically administering to the skin of the subject a composition comprising a solvent and a volatile anesthetic in an amount effective to reduce pain, wherein:
   (i) the solvent is at least one selected from the group consisting of dimethylsulfoxide, dimethylformamide, dimethylacetamide, N-methyl-2-pyrollidone, dimethylisosorbide, ethanol, propanol and isopropanol,
   (ii) the solvent is present in an amount effective to reduce the vapor pressure of the volatile anesthetic,
   (iii) the volatile anesthetic is in an emulsion, a liposome suspension, or a microdroplet suspension,
   (iv) the volatile anesthetic is at least one selected from the group consisting of isoflurane, halothane, enflurane, sevoflurane, desflurane and methoxyflurane, and
   (v) administration of the volatile anesthetic to the skin of the subject reduces pain in the subject.

2. The method of claim 1, wherein the subject is a human patient or an animal patient.

3. The method of claim 1, wherein the volatile anesthetic is dissolved in a solution, and wherein the composition further comprises a solubilizing agent selected from the group consisting of cyclodextrin, human serum albumin, propylene glycol, perfluorooctyl bromide, and perfluorocarbon.

4. The method of claim 1, wherein the volatile anesthetic is in the microdroplet suspension, wherein the microdroplet suspension comprises a sphere of the volatile anesthetic surrounded by a stabilizing layer of lipid.

5. The method of claim 1, wherein the volatile anesthetic is dissolved in a solution comprising the solvent, wherein the solution is a component of the emulsion.

6. The method of claim 1, wherein the volatile anesthetic is isoflurane.

* * * * *

UNITED STATES PATENT AND TRADEMARK OFFICE
CERTIFICATE OF CORRECTION

PATENT NO. : 9,566,251 B2
APPLICATION NO. : 13/722880
DATED : February 14, 2017
INVENTOR(S) : Allen Burton et al.

Page 1 of 2

It is certified that error appears in the above-identified patent and that said Letters Patent is hereby corrected as shown below:

On the Title Page

Item (56) References Cited - Other Publications, insert:
--Anderson et al., "Isoflurane blocks LTP of hippocampal CA1 neurons at concentrations that block recalling drug anesthesia," Society of Neuroscience Abstracts, XP002477753, 2000.
Ardente et al., "Vehicle effects on in vitro transdermal absorption of sevolurane in the bullfrog, Rana catesbeiana," Environmental Toxicology and Pharmacology, 25:373-379, 2008.
Chai et al., "Epidural anaesthetic effect of the 8% emulsified isoflurane: a study in rabbits," British Journal of Anaesthesia, 100(1):109-115, 2008.
Extended European Search Report and Search Opinion issued in European Application No. EP 09704014, mailed February 9, 2011.
Fast et al., "Fluoropolymer-based emulsions for the intravenous delivery of sevoflurane," Anesthesiology, 109:651-6, 2008.
Haynes et al., "Ultra-Long Duration Local Anesthesia Produced by Intra-Dermal Injection of Lecithin-Coated Methoxyflurane Microdroplets," Proceed. Intern. Symp. Control Rei. Bioact. Meter, 14:293-294, 1987.
Haynes et al., "Ultra-Long-Duration Local Anesthesia Produced by Injection of Lecithin-Coated Methoxyflurane Microdroplets," Anesthesiology, 63:490-499, 1985.
Itah et al., "A replacement for methoxyflurane (Metofane) in open-circuit anesthesia," Laboratory Animals, 38:280-285, 2004.
Kirkpatrick et al., "Long Duration Local Anesthesia with Lecithin-Coated Microdroplets of Methoxyflurane: Studies Rat Skin," Regional Anesthesia, 16:164-172, 1991.
Mathias et al., "Intravenous Isoflurane in Lipid Emulsion Promotes Cardiovascular and Respiratory Stability Experimental Model," Rev. Bras Anestesiol, 54(5):650-662, 2004.
Matute et al., "Characterisation of sevoflurane effects on spinal somato-motor nociceptive and non-nociceptive transmission in neonatal rat spinal cord: an electrophysiological study in vitro," Neuro Pharmacology, 44:811-816, 2003.

Signed and Sealed this
Eighteenth Day of July, 2017

Joseph Matal
*Performing the Functions and Duties of the
Under Secretary of Commerce for Intellectual Property and
Director of the United States Patent and Trademark Office*

Parlato et al., "Synthesis, characterization, and applications of hemifluorinated dibranced amphiphiles," J. Org. Chem., 76:6584-6591, 2011.
Petersen-Felix et al., "Analgesic effect in humans of subanaesthetic isoflurane concentrations evaluated by experimentally induced pain," British Journal of Anaesthesia, 75:55-60, 1995.
Rao et al., "Emulsified Isoflurane Produces Cardiac Protection After Ischemia-Reperfusion Injury in Rabbits," Depart of Anesthesiology, Vol. 106, No. 5, 2008.
Rasmussen et al., "Does Anaesthesia cause postoperative cognitive dysfunction? A randomized study of regional versus general anaesthesia in 438 elderly patients," Acta Anaesthesiol Scand, 47:260-266, 2003.
Wu et al., "Pharmacokinetics of Methoxyflurane After Its Intra-Dermal Injection as Lecithin-Coated Microdroplets," Journal of Controlled Release, 9:1-12, 1989.
Zou et al., "The Efficacy and Safety of Intravenous Emulsified Isoflurane in Rats," Anesth Analg, 102:129-134, 2006.--.